US012606549B2

(12) United States Patent
Xiong et al.

(10) Patent No.: US 12,606,549 B2
(45) Date of Patent: Apr. 21, 2026

(54) ANTICHOLINERGIC AGENTS

(71) Applicant: REZUBIO PHARMACEUTICALS CO., LTD, Zhuhai (CN)

(72) Inventors: Yusheng Xiong, Zhuhai (CN); Hongping Guan, Zhuhai (CN)

(73) Assignee: REZUBIO PHARMACEUTICALS CO., LTD, Zhuhai (CN)

( * ) Notice: Subject to any disclaimer, the term of this patent is extended or adjusted under 35 U.S.C. 154(b) by 399 days.

(21) Appl. No.: 18/254,405

(22) PCT Filed: Nov. 24, 2021

(86) PCT No.: PCT/CN2021/132671

§ 371 (c)(1),
(2) Date: May 25, 2023

(87) PCT Pub. No.: WO2022/111500

PCT Pub. Date: Jun. 2, 2022

(65) Prior Publication Data

US 2024/0002372 A1 Jan. 4, 2024

(30) Foreign Application Priority Data

Nov. 26, 2020 (WO) ................ PCT/CN2020/131836

(51) Int. Cl.
*C07D 413/12* (2006.01)
*C07D 207/08* (2006.01)
*C07D 207/12* (2006.01)

(52) U.S. Cl.
CPC ......... *C07D 413/12* (2013.01); *C07D 207/08* (2013.01); *C07D 207/12* (2013.01)

(58) Field of Classification Search
CPC ... C07D 413/12; C07D 207/08; C07D 207/12
See application file for complete search history.

(56) References Cited

U.S. PATENT DOCUMENTS 2,956,062 A 10/1960 Lunsford et al.
3,301,869 A 1/1967 Lunsford et al.
7,504,432 B2 * 3/2009 Ogino ..................... A61P 11/00 514/429
10,100,012 B2 10/2018 Dugar et al.
11,414,406 B2 8/2022 Lindsley et al.
2002/0173536 A1 11/2002 Noe et al.
2009/0028873 A1 * 1/2009 Gant ..................... C07C 217/74 514/646
2018/0186735 A1 7/2018 Shaw et al.

FOREIGN PATENT DOCUMENTS

CN 106659697 5/2017
CN 111788182 10/2020
JP 2017522366 8/2017

OTHER PUBLICATIONS

Di, Int J Pharm, vol. 297, 2005, 110-119. (Year: 2005).*
Hill, Anal Chem, 200, vol. 0, 5574-5582. (Year: 2008).*
Wu, Pyrrolidines I, vol. 26, 1961, 1519-1524. (Year: 1961).*
Wu, Pyrrolidines II, 1524-1528, vol. 26, 1960. (Year: 1960).*
Yamashita ey al., "Chemical modification-mediated optimisation of bronchodilatory activity of mepenzolate, a muscarinic receptor antagonist with anti-inflammatory activity", Bioorganic & Medicinal Chemistry, 2019, pp. 3339-3346.
Registry Copyright 2022 ACS on STN, CAS "1834577-91-1", STN, pp. 1-73.
Doyle et al., "Pharmacodynamic Compounds. Part I. Some. Antispasmodics derived from Substituted 2-Pyrrolidinylallccenols", Jan. 1, 1958, Downloaded by State Intellectual Property Office of P.R.C. on Apr. 7, 2024, pp. 4458-4466.
Ryan et al., "The Synthesis and Anticholinergic Activity of Ester and Amiddler-ivatives of 2-Substituted Piperidines", Derivatives of 2-Substituted Piperidines, May 1961, vol. 26, pp. 1547-1550.

* cited by examiner

*Primary Examiner* — D Margaret M Seaman
(74) *Attorney, Agent, or Firm* — NIXON & VANDERHYE, PC

(57) ABSTRACT

Compounds shown in Formula (I), pharmaceutical compositions, and methods of using related to muscarinic acetylcholine receptors. The compounds herein are typically muscarinic acetylcholine receptor antagonists, such as $M_3$ antagonists, which can be used for treating a variety of disorders, conditions or diseases such as hyperhidrosis.

(I)

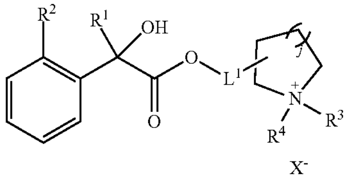

19 Claims, No Drawings

ANTICHOLINERGIC AGENTS

This application is the U.S. national phase of International Application No. PCT/CN2021/132671, filed Nov. 24, 2021, which designated the U.S. and claims priority to International Application No. PCT/CN2020/131836, filed Nov. 26, 2020, the entire contents of each of which are herein incorporated by reference.

In various embodiments, the present disclosure generally relates to novel compounds, pharmaceutical compositions, methods of preparing and methods of using the same, such as to provide an anticholinergic effect.

BACKGROUND

Muscarinic acetylcholine receptors, or mAChRs, are acetylcholine receptors that form G protein-coupled receptor complexes in cell membranes. Five subtypes of muscarinic receptors have been determined, named $M_1$-$M_5$, with $M_1$, $M_3$, $M_5$ receptors are coupled with $G_q$ proteins, while $M_2$ and $M_4$ receptors are coupled with $G_{i/o}$ protein. mAChRs are widely expressed in different tissues and cells, and regulate many important functions of the central and peripheral nervous system. In bladder, $M_2$ and $M_3$ receptors are predominantly expressed in detrusor muscle of various species. Both $M_1$ and $M_3$ receptors are expressed in the salivary glands, sweat glands, apocrine glands, sublingual glands, and lacrimal glands, whereas $M_3$ receptors are predominantly expressed in the parotid glands. In gastrointestinal tract, $M_2$ and $M_3$ receptors are both expressed in the smooth muscle, and $M_3$ receptors are thought to play important role in cholinergic stimulation of gastrointestinal motility. In the brain, $M_3$ receptors are low whereas $M_1$, $M_2$, $M_4$, and $M_5$ receptors are expressed abundantly in different areas. $M_1$ and $M_4$ receptors are expressed in human eye. $M_2$ and $M_3$ receptors are expressed in human heart and regulate heart rate and cardiac functions. Muscarinic anticholinergic agents have been used for treating a variety of different diseases or disorders, such as diarrhea, allergies, asthma, atrial fibrillation with bradycardia, motion sickness, anxiety, hyperhidrosis, low heart rate, overactive bladder, respiratory problems such as asthma and COPD, and neurological problems such as Parkinson's disease and Alzheimer's disease.

Various muscarinic acetylcholine receptor antagonists are reported, such as the naturally occurring atropine and scopolamine and a variety of synthetic agents, such as homatropine and eucatropine, etc. However, new muscarinic antagonists are still needed for various indications.

BRIEF SUMMARY

In various embodiments, the present disclosure is based in part on the novel compounds/salts that may provide an anticholinergic effect, more particularly, as muscarinic acetylcholine receptor antagonists.

Some embodiments of the present disclosure are directed to salts of Formula I:

Formula I

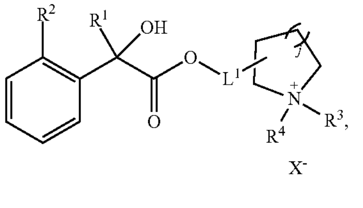

wherein the variables $R^1$, $R^2$, $R^3$, $R^4$, $L^1$, $X^-$, and j are defined herein. In some embodiments, the present disclosure provides a salt of a subformula of Formula I, such as Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, or I-6 as described herein. The salts of Formula I herein are typically muscarinic receptor antagonists. The salts of Formula I can be typically prepared from a corresponding compound of Formula II:

Formula II

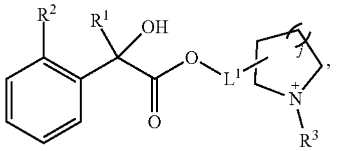

wherein the variables $R^1$, $R^2$, $R^3$, $L^1$, and j are defined herein. In some embodiments, the present disclosure also provides a pharmaceutically acceptable salt of the compound of Formula II (e.g., Formula II-1 or II-2).

Certain embodiments of the present disclosure are directed to a pharmaceutical composition comprising one or more of the compounds/salts of the present disclosure (e.g., a compound/salt of Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, or I-6), any of Examples 1-12, or any of the salts shown in Table 1 or 2 herein, or a pharmaceutically acceptable salt thereof) and optionally a pharmaceutically acceptable excipient. The pharmaceutical composition described herein can be formulated for different routes of administration, such as for oral administration, parenteral administration, topical administration, inhalation, eye drops etc. For example, in some embodiments, the pharmaceutical composition can be formulated for topical administration, such as in the form of a topical solution, cream, ointment, mousse, gel, lotion, or powder.

Some embodiments of the present disclosure are directed to a method of treating or preventing a disorder, condition or disease that may be responsive to the antagonism of mAChRs, such as $M_3$ receptor, in a subject in need thereof. In some embodiments, the method comprises administering to the subject an effective amount of a compound of the present disclosure (e.g., a compound/salt of Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, or I-6), any of Examples 1-12, or any of the salts shown in Table 1 or 2 herein, or a pharmaceutically acceptable salt thereof) or an effective amount of a pharmaceutical composition described herein.

Some embodiments of the present disclosure are directed to a method of inhibiting the activity of mAChRs such as $M_3$ receptor in a subject or biological sample. In some embodiments, the method comprises contacting the mAChRs such as $M_3$ receptor with an effective amount of a compound of the present disclosure (e.g., a compound/salt of Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, or I-6), any of Examples 1-12, or any of the salts shown in Table 1 or 2 herein, or a pharmaceutically acceptable salt thereof) or an effective amount of a pharmaceutical composition described herein.

In some particular embodiments, the present disclosure provides a method of treating hyperhidrosis in a subject in need thereof. In some embodiments, the method comprises administering to the subject a therapeutically effective amount of a compound of the present disclosure (e.g., a compound/salt of Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, or I-6), any of Examples 1-12, or any of the salts shown in Table 1 or 2 herein, or a pharmaceutically acceptable salt thereof) or an effective amount of a pharmaceutical composition described herein. Typically, the administering is through the topical route. In some embodiments, one or more compounds/salts of the present disclosure can be administered as the only active ingredient(s). In some embodiments, one or more compounds of the present disclosure can be used in combination with an additional therapy, e.g., additional therapy that is effective in treating hyperhidrosis.

It is to be understood that both the foregoing summary and the following detailed description are exemplary and explanatory only, and are not restrictive of the invention herein.

DETAILED DESCRIPTION

The present disclosure generally relates to compounds that are useful as muscarinic anticholinergics. The compounds herein can typically be used for treating or preventing various diseases or disorders mediated by such muscarinic cholinergic receptors described herein, such as those mediated by $M_3$ receptor.

Compounds

Formula I

In some embodiments, the present disclosure provides a salt of Formula I:

Formula I

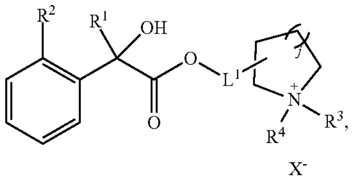

wherein.

$X^-$ is a counterion;

$R^1$ is hydrogen or an optionally substituted $C_{3-8}$ carbocyclyl;

$L^1$ is null, $C_{1-4}$ alkylene, or $C_{1-4}$ heteroalkylene;

$R^2$ is hydrogen, $C_{1-6}$ alkyl, $C_{2-6}$ alkenyl, $C_{2-6}$ alkynyl, $C_{3-8}$ carbocyclyl, 4-8 membered heterocyclyl, phenyl, or 5-10 membered heteroaryl, each of which is optionally substituted;

$R^3$ and $R^4$ are each independently hydrogen or $C_{1-6}$ alkyl; and j is 0, 1 or 2.

In some embodiments, the salt of Formula I (including any of the applicable sub-formulae as described herein) can comprise one or more asymmetric centers and/or axial chirality, and thus can exist in various stereoisomeric forms, e.g., enantiomers and/or diastereomers. In some embodiments, the salt of Formula I can exist in the form of an individual enantiomer and/or diastereomer, as applicable, or a mixture of stereoisomers, including racemic mixtures and mixtures enriched in one or more stereoisomers. In some embodiments, when applicable, the salt of Formula I (including any of the applicable sub-formulae as described herein) can exist as an isolated individual enantiomer substantially free (e.g., with less than 20%, less than 10%, less than 5%, less than 1%, by weight, by HPLC area, or both, or with a non-detectable amount) of the other enantiomer. In some embodiments, when applicable, the salt of Formula I (including any of the applicable sub-formulae as described herein) can exist as an isolated individual diastereomer substantially free (e.g., with less than 20%, less than 10%, less than 5%, less than 1%, by weight, by HPLC area, or both, or with a non-detectable amount) of the other diastereomer(s). In some embodiments, when applicable, the salt of Formula I (including any of the applicable sub-formulae as described herein) can also exist as a mixture of stereoisomers in any ratio, such as a racemic mixture.

In some embodiments, the salt of Formula I can have a Formula I-1:

Formula I-1

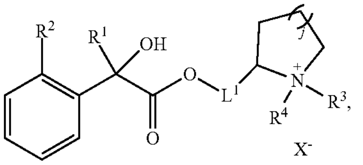

wherein the variables include any of those described herein in any combination.

In some embodiments, the salt of Formula I-1 can have a Formula I-1-E1 or Formula I-1-E2:

Formula I-1-E1

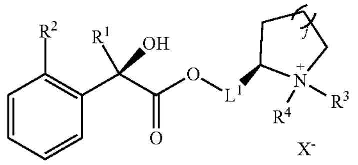

Formula I-1-E2

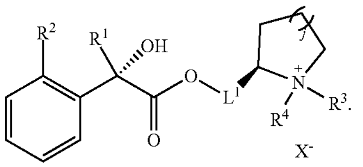

In some embodiments, the salt of Formula I-1 can have a Formula I-1-E3 or Formula I-1-E4:

Formula I-1-E3

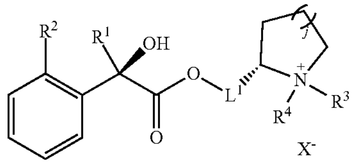

-continued

Formula I-1-E4

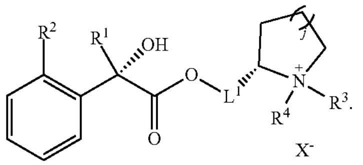

In some embodiments, the salt of Formula I-1 can be a substantially pure stereoisomer having Formula I-1-E1, which can be substantially free of any of the corresponding isomeric forms Formula I-1-E2, Formula I-1-E3, and Formula I-1-E4. For example, in some embodiments, out of the four possible stereoisomers, the combined amount of Formula I-1-E2, Formula I-1-E3, and Formula I-1-E4 that may be present is less than 20%, less than 10%, less than 5%, less than 1%, by weight, by HPLC area, or both, or none of Formula I-1-E2, Formula I-1-E3, and Formula I-1-E4 is detectable. In some embodiments, the salt of Formula I-1 can be a substantially pure stereoisomer having Formula I-1-E2, which can be substantially free of any of the corresponding isomeric forms Formula I-1-E1, Formula I-1-E3, and Formula I-1-E4. For example, in some embodiments, out of the four possible stereoisomers, the combined amount of Formula I-1-E1, Formula I-1-E3, and Formula I-1-E4 that may be present is less than 20%, less than 10%, less than 5%, less than 1%, by weight, by HPLC area, or both, or none of Formula I-1-E1, Formula I-1-E3, and Formula I-1-E4 is detectable. In some embodiments, the salt of Formula I-1 can be a substantially pure stereoisomer having Formula I-1-E3, which can be substantially free of any of the corresponding isomeric forms Formula I-1-E1, Formula I-1-E2, and Formula I-1-E4. For example, in some embodiments, out of the four possible stereoisomers, the combined amount of Formula I-1-E1, Formula I-1-E2, and Formula I-1-E4 that may be present is less than 20%, less than 10%, less than 5%, less than 1%, by weight, by HPLC area, or both, or none of Formula I-1-E1, Formula I-1-E2, and Formula I-1-E4 is detectable. In some embodiments, the salt of Formula I-1 can be a substantially pure stereoisomer having Formula I-1-E4, which can be substantially free of any of the corresponding isomeric forms Formula I-1-E1, Formula I-1-E2, and Formula I-1-E3. For example, in some embodiments, out of the four possible stereoisomers, the combined amount of Formula I-1-E1, Formula I-1-E2, and Formula I-1-E3 that may be present is less than 20%, less than 10%, less than 5%, less than 1%, by weight, by HPLC area, or both, or none of Formula I-1-E1, Formula I-1-E2, and Formula I-1-E3 is detectable. In some embodiments, a given salt of Formula I-1 can be present in the form of a mixture of any two or more of the four possible stereoisomers Formula I-1-E1, I-1-E2, I-1-E3, and I-1-E4, in any ratio.

In some embodiments, the salt of Formula I can have a Formula I-2:

Formula I-2

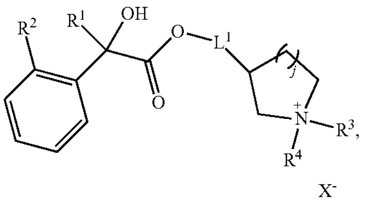

wherein the variables include any of those described herein in any combination.

In some embodiments, the salt of Formula I-2 can have a Formula I-2-E1 or Formula I-2-E2:

Formula I-2-E1

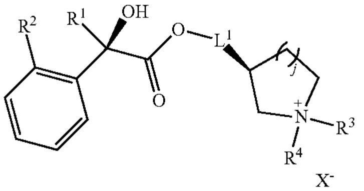

Formula I-2-E2

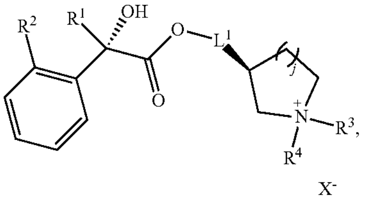

In some embodiments, the salt of Formula I-2 can have a Formula I-2-E3 or Formula I-2-E4:

Formula I-2-E3

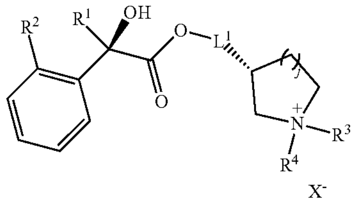

Formula I-2-E4

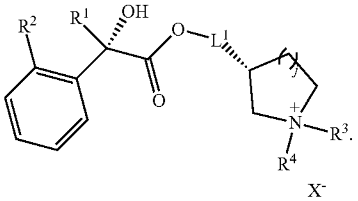

In some embodiments, the salt of Formula I-2 can be a substantially pure stereoisomer having Formula I-2-E1, which can be substantially free of any of the corresponding isomeric forms Formula I-2-E2, Formula I-2-E3, and Formula I-2-E4. For example, in some embodiments, out of the four possible stereoisomers, the combined amount of Formula I-2-E2, Formula I-2-E3, and Formula I-2-E4 that may be present is less than 20%, less than 10%, less than 5%, less than 1%, by weight, by HPLC area, or both, or none of Formula I-2-E2, Formula I-2-E3, and Formula I-2-E4 is detectable. In some embodiments, the salt of Formula I-2 can be a substantially pure stereoisomer having Formula I-2-E2, which can be substantially free of any of the corresponding isomeric forms Formula I-2-E1, Formula I-2-E3, and Formula I-2-E4. For example, in some embodiments, out of the four possible stereoisomers, the combined amount of Formula I-2-E1, Formula I-2-E3, and Formula I-2-E4 that may be present is less than 20%, less than 10%, less than 5%, less than 1%, by weight, by HPLC area, or both, or none of Formula I-2-E1, Formula I-2-E3, and Formula I-2-E4 is detectable. In some embodiments, the salt of Formula I-2 can be a substantially pure stereoisomer having Formula I-2-E3, which can be substantially free of any of the corresponding isomeric forms Formula I-2-E1, Formula I-2-E2, and Formula I-2-E4. For example, in some embodiments, out of the four possible stereoisomers, the combined amount of Formula I-2-E1, Formula I-2-E2, and Formula I-2-E4 that may be present is less than 20%, less than 10%, less than 5%, less than 1%, by weight, by HPLC area, or both, or none of Formula I-2-E1, Formula I-2-E2, and Formula I-2-E4 is detectable. In some embodiments, the salt of Formula I-2 can be a substantially pure stereoisomer having Formula I-2-E4, which can be substantially free of any of the corresponding isomeric forms Formula I-2-E1, Formula I-2-E2, and Formula I-2-E3. For example, in some embodiments, out of the four possible stereoisomers, the combined amount of Formula I-2-E1, Formula I-2-E2, and Formula I-2-E3 that may be present is less than 20%, less than 10%, less than 5%, less than 1%, by weight, by HPLC area, or both, or none of Formula I-2-E1, Formula I-2-E2, and Formula I-2-E3 is detectable. In some embodiments, the salt of Formula I-2 can be present in the form of a mixture of any two or more of the four possible stereoisomers Formula I-2-E1, I-2-E2, I-2-E3, and I-2-E4, in any ratio.

Typically, j in Formula I (e.g., Formula I-1, I-1-E1, I-1-E2, I-1-E3, I-1-E4, I-2, I-2-E1, I-2-E2, I-2-E3, I-2-E4) is 0, 1, or 2. Preferably, j in Formula I (e.g., Formula I-1, I-1-E1, I-1-E2, I-1-E3, I-1-E4, I-2, I-2-E1, I-2-E2, I-2-E3, I-2-E4) is 1. For example, in some embodiments, the salt of Formula I can be characterized as having a Formula I-3 or I-4:

Formula I-3

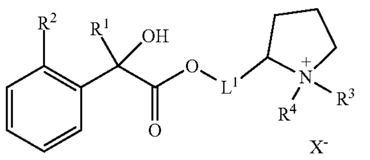

Formula I-4

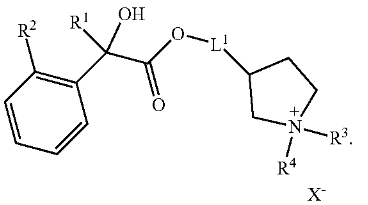

In some embodiments, the salt of Formula I-3 can have a Formula I-3-E1 or Formula I-13-E2:

Formula I-3-E1

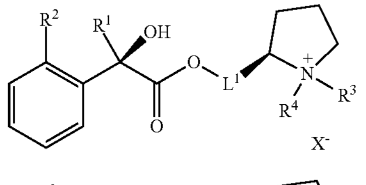

Formula I-3-E2

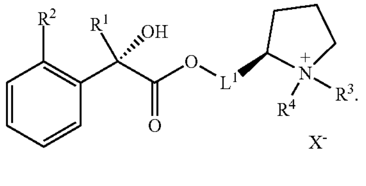

In some embodiments, the salt of Formula I-3 can have a Formula I-3-E3 or Formula I-3-E4:

Formula I-3-E3

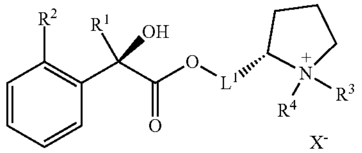

Formula I-3-E4

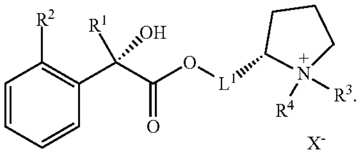

In some embodiments, the salt of Formula I-3 can be a substantially pure stereoisomer having Formula I-3-E1, which can be substantially free of any of the corresponding isomeric forms Formula I-3-E2, Formula I-3-E3, and Formula I-3-E4. For example, in some embodiments, out of the four possible stereoisomers, the combined amount of Formula I-3-E2, Formula I-3-E3, and Formula I-3-E4 that may be present is less than 20%, less than 10%, less than 5%, less than 1%, by weight, by HPLC area, or both, or none of Formula I-3-E2, Formula I-3-E3, and Formula I-3-E4 is detectable. In some embodiments, the salt of Formula I-3 can be a substantially pure stereoisomer having Formula I-3-E2, which can be substantially free of any of the corresponding isomeric forms Formula I-3-E1, Formula I-3-E3, and Formula I-3-E4. For example, in some embodiments, out of the four possible stereoisomers, the combined amount of Formula I-3-E1, Formula I-3-E3, and Formula I-3-E4 that may be present is less than 20%, less than 10%, less than 5%, less than 1%, by weight, by HPLC area, or both, or none of Formula I-3-E1, Formula I-3-E3, and Formula I-3-E4 is detectable. In some embodiments, the salt of Formula I-3 can be a substantially pure stereoisomer having Formula I-3-E3, which can be substantially free of any of the corresponding isomeric forms Formula I-3-E1, Formula I-3-E2, and Formula I-3-E4. For example, in some embodiments, out of the four possible stereoisomers, the combined amount of Formula I-3-E1, Formula I-3-E2, and Formula I-3-E4 that may be present is less than 20%, less than 10%, less than 5%, less than 1%, by weight, by HPLC area, or both, or none of Formula I-3-E1, Formula I-3-E2, and Formula I-3-E4 is detectable. In some embodiments, the salt of Formula I-3 can be a substantially pure stereoisomer having Formula I-3-E4, which can be substantially free of any of the corresponding isomeric forms Formula I-3-E1, Formula I-3-E2, and Formula I-3-E3. For example, in some embodiments, out of the four possible stereoisomers, the combined amount of Formula I-3-E1, Formula I-3-E2, and Formula I-3-E3 that may be present is less than 20%, less than 10%, less than 5%, less than 1%, by weight, by HPLC area, or both, or none of Formula I-3-E1, Formula I-3-E2, and Formula I-3-E3 is detectable. In some embodiments, the salt of Formula I-3 can be present in the form of a mixture of any two or more of the four possible stereoisomers Formula I-3-E1, I-3-E2, I-3-E3, and I-3-E4, in any ratio.

In some embodiments, the salt of Formula I-4 can have a Formula I-4-E1 or Formula I-4-E2:

Formula I-4-E1

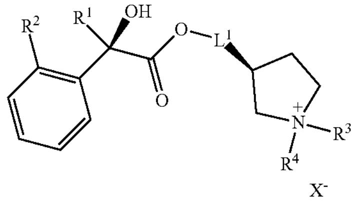

Formula I-4-E2

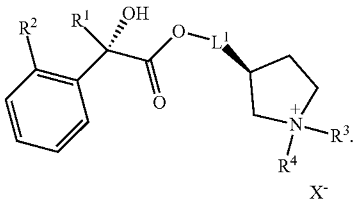

In some embodiments, the salt of Formula I-4 can have a Formula I-4-E3 or Formula I-4-E4:

Formula I-4-E3

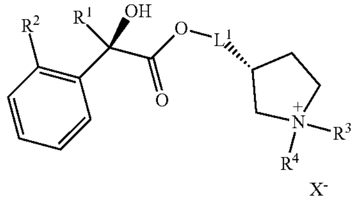

Formula I-4-E4

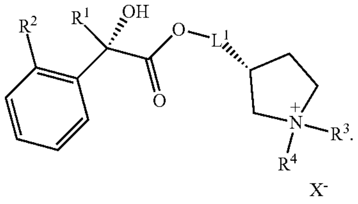

In some embodiments, the salt of Formula I-4 can be a substantially pure stereoisomer having Formula I-4-E1, which can be substantially free of any of the corresponding isomeric forms Formula I-4-E2, Formula I-4-E3, and Formula I-4-E4. For example, in some embodiments, out of the four possible stereoisomers, the combined amount of Formula I-4-E2, Formula I-4-E3, and Formula I-4-E4 that may be present is less than 20%, less than 10%, less than 5%, less than 1%, by weight, by HPLC area, or both, or none of Formula I-4-E2, Formula I-4-E3, and Formula I-4-E4 is detectable. In some embodiments, the salt of Formula I-4 can be a substantially pure stereoisomer having Formula I-4-E2, which can be substantially free of any of the corresponding isomeric forms Formula I-4-E1, Formula I-4-E3, and Formula I-4-E4. For example, in some embodiments, out of the four possible stereoisomers, the combined amount of Formula I-4-E1, Formula I-4-E3, and Formula I-4-E4 that may be present is less than 20%, less than 10%, less than 5%, less than 1%, by weight, by HPLC area, or both, or none of Formula I-4-E1, Formula I-4-E3, and Formula I-4-E4 is detectable. In some embodiments, the salt of Formula I-4 can be a substantially pure stereoisomer having Formula I-4-E3, which can be substantially free of any of the corresponding isomeric forms Formula I-4-E1, Formula I-4-E2, and Formula I-4-E4. For example, in some embodiments, out of the four possible stereoisomers, the combined amount of Formula I-4-E1, Formula I-4-E2, and Formula I-4-E4 that may be present is less than 20%, less than 10%, less than 5%, less than 1%, by weight, by HPLC area, or both, or none of Formula I-4-E1, Formula I-4-E2, and Formula I-4-E4 is detectable. In some embodiments, the salt of Formula I-4 can be a substantially pure stereoisomer having Formula I-4-E4, which can be substantially free of any of the corresponding isomeric forms Formula I-4-E1, Formula I-4-E2, and Formula I-4-E3. For example, in some embodiments, out of the four possible stereoisomers, the combined amount of Formula I-4-E1, Formula I-4-E2, and Formula I-4-E3 that may be present is less than 20%, less than 10%, less than 5%, less than 1%, by weight, by HPLC area, or both, or none of Formula I-4-E1, Formula I-4-E2, and Formula I-4-E3 is detectable. In some embodiments, the salt of Formula I-4 can be present in the form of a mixture of any two or more of the four possible stereoisomers Formula I-4-E1, I-4-E2, I-4-E3, and I-4-E4, in any ratio.

In some embodiments, $L^1$ in Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4,) can be null, in which case, the C(O)—O group in Formula I is directly linked to the nitrogen containing ring of Formula I.

In some embodiments, $L^1$ in Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4,) can be a $C_{1-4}$ alkylene, such as $CH_2$.

In some preferred embodiments, $L^1$ in Formula I-1, I-1-E1, I-1-E2, I-1-E3, I-1-E4, I-3, I-3-E1, I-3-E2, I-3-E3, or I-3-E4 is $CH_2$. For example, in some embodiments, the salt of Formula I-1, I-1-E1, I-1-E2, I-1-E3, I-1-E4, I-3, I-3-E1, I-3-E2, I-3-E3, or I-3-E4 can be characterized as having a Formula I-5:

Formula I-5

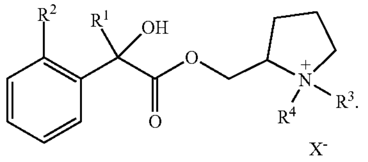

In some preferred embodiments, $L^1$ in Formula 1-2, I-2-E1, I-2-E2, I-2-E3, I-2-E4, I-4, I-4-E1, I-4-E2, I-4-E3, or I-4-E4 is null, and $R^1$ is hydrogen. For example, in some embodiments, the salt of Formula I-2, I-2-E1, I-2-E2, I-2-E3, I-2-E4, I-4, I-4-E1, I-4-E2, I-4-E3, or I-4-E4 can be characterized as having a Formula I-6:

Formula I-6

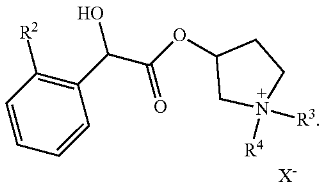

Typically, $R^1$ in Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5) is hydrogen.

In some embodiments, $R^1$ in Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5) can also be an optionally substituted $C_{3-8}$ carbocyclyl, such as cyclopentyl.

Various groups are suitable as $R^2$ for Formula I. Typically, $R^2$ in Formula I is not hydrogen. However, in some embodiments, $R^2$ in Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, I-6) can also be hydrogen. When $R^2$ in Formula I is hydrogen, $R^1$ typically is not hydrogen.

In some embodiments, $R^2$ in Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, I-6) can be an optionally substituted $C_{1-6}$ alkyl. For example, in some embodiments, $R^2$ can be a $C_{1-6}$ alkyl, which is optionally substituted with one or more (e.g., 1, 2, or 3) substituents independently selected from F, OH, $R^A$, $OR^A$, and phenyl, wherein the phenyl is optionally substituted with one or more (e.g., 1, 2, or 3) substituents independently selected from halogen (e.g., F or Cl), OH, $C_{1-4}$ alkyl, fluorine-substituted $C_{1-4}$ alkyl, $C_{1-4}$ alkoxy, and fluorine-substituted $C_{1-4}$ alkoxy, wherein $R^A$ at each occurrence is independently a $C_{1-4}$ alkyl or $C_{3-6}$ cycloalkyl, which is optionally substituted with one or more (e.g., 1, 2, or 3) substituents independently selected from F, OH, $C_{1-4}$ alkyl, fluorine-substituted $C_{1-4}$ alkyl, $C_{1-4}$ alkoxy, and fluorine-substituted $C_{1-4}$ alkoxy. In some embodiments, $R^2$ can be a $C_{3-6}$ alkyl, e.g., a branched $C_{3-6}$ alkyl, such as isopropyl.

In some embodiments, $R^2$ in Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, I-6) can be an optionally substituted $C_{3-8}$ carbocyclyl.

In some preferred embodiments, $R^2$ in Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, I-6) can be an optionally substituted $C_{3-6}$ cycloalkyl, such as cyclopropyl, cyclobutyl, cyclopentyl, or cyclohexyl. For example, in some embodiments, $R^2$ can be a $C_{3-6}$ cycloalkyl, which is optionally substituted with one or more (e.g., 1, 2, or 3) substituents independently selected from F, OH, $R^A$, and $OR^A$, wherein $R^A$ at each occurrence is independently a $C_{1-4}$ alkyl or $C_{3-6}$ cycloalkyl, which is optionally substituted with one or more (e.g., 1, 2, or 3) substituents independently selected from F, OH, $C_{1-4}$ alkyl, fluorine-substituted $C_{1-4}$ alkyl, $C_{1-4}$ alkoxy, and fluorine-substituted $C_{1-4}$ alkoxy. In some embodiments, $R^2$ in Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, I-6) can be cyclopropyl, cyclobutyl, cyclopentyl, or cyclohexyl, more preferably, cyclopentyl.

In some preferred embodiments, $R^2$ in Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, I-6) can be an optionally substituted $C_{4-7}$ cycloalkenyl, e.g., having one carbon-carbon double bond in the ring. For example, in some embodiments, $R^2$ can be a $C_{4-7}$ cycloalkenyl, which can be optionally substituted with one or more (e.g., 1, 2, or 3) substituents independently selected from F, OH, $R^A$, and $OR^A$, wherein $R^A$ at each occurrence is independently a $C_{1-4}$ alkyl or $C_{3-6}$ cycloalkyl, which is optionally substituted with one or more (e.g., 1, 2, or 3) substituents independently selected from F, OH, $C_{1-4}$ alkyl, fluorine-substituted $C_{1-4}$ alkyl, $C_{1-4}$ alkoxy, and fluorine-substituted $C_{1-4}$ alkoxy. In some embodiments, $R^2$ in Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, I-6) can be cyclopentenyl, preferably,

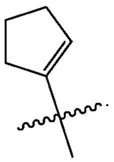

In some embodiments, $R^2$ in Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, I-6) can be an optionally substituted phenyl. For example, in some embodiments, $R^2$ can be phenyl, which is optionally substituted with one or more (e.g., 1, 2, or 3) substituents independently selected from F, Cl, OH, $C_{1-4}$ alkyl, fluorine-substituted $C_{1-4}$ alkyl, $C_{1-4}$ alkoxy, and fluorine-substituted $C_{1-4}$ alkoxy. In some embodiments, $R^2$ in Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, I-6) can be phenyl.

In some embodiments, $R^2$ in Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, I-6) can be an optionally substituted 5- or 6-membered heteroaryl having 1-4 ring heteroatoms independently selected from N, O, and S, e.g., those described herein. In some embodiments, $R^2$ in Formula I can be an optionally substituted 5-membered heteroaryl having 1-3 ring heteroatoms independently selected from N, O, and S, such as oxazolyl, thiazolyl, etc. In some embodiments, the 5-membered heteroaryl can be optionally substituted with one or more (e.g., 1, 2, or 3) substituents independently selected from F, Cl, OH, $C_{1-4}$ alkyl, fluorine-substituted $C_{1-4}$ alkyl, $C_{1-4}$ alkoxy, and fluorine-substituted $C_{1-4}$ alkoxy. In some embodiments, $R^2$ in Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, I-6) can be oxazolyl, such as

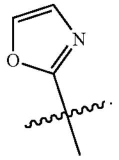 [SMILES: *c1ncco1]

In some embodiments, $R^2$ in Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, I-6) can be an optionally substituted 6-membered heteroaryl having 1-2 ring heteroatoms independently selected from N, O, and S, e.g., as disclosed herein, such as pyridyl or pyrimidinyl, etc. In some embodiments, the 6-membered heteroaryl can be optionally substituted with one or more (e.g., 1, 2, or 3) substituents independently selected from F, Cl, OH, $C_{1-4}$ alkyl, fluorine-substituted $C_{1-4}$ alkyl, $C_{1-4}$ alkoxy, and fluorine-substituted $C_{1-4}$ alkoxy.

Typically, $R^3$ in Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, I-6) is a $C_{1-6}$ alkyl, more preferably, methyl.

Typically, $R^4$ in Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, I-6) is a $C_{1-6}$ alkyl, more preferably, methyl.

The counterion $X^-$ in Formula I is not particularly limited, as the anticholinergic activity of the salts of Formula I does not rely on the identity of $X^-$. Typically, $X^-$ in Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, I-6) is a pharmaceutically acceptable counterion, for example, a halide (e.g., $F^-$, $Cl^-$, $Br^-$, or $I^-$). Other suitable counterions include those derived from various inorganic acids or organic acids, such as sulfuric acid, nitric acid, phosphoric acid, acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. It should be understood that in some embodiments, $X^-$ can also derive from a multivalent anion, which is counterbalanced with the cationic structure shown in Formula I so that the overall charge of X is negative 1.

In some embodiments, the present disclosure also provides a salt selected from those shown in Table 1 below:

TABLE 1

| List of Exemplary Salts of the Present Disclosure |
|---|
| 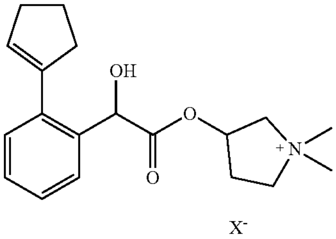 |
| 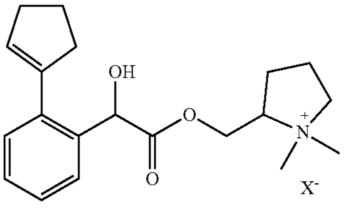 |
| 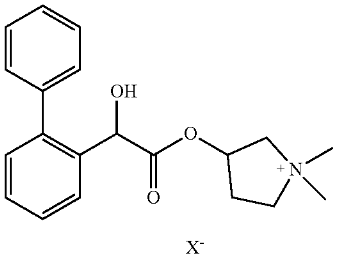 |

TABLE 1-continued

| List of Exemplary Salts of the Present Disclosure |
|---|
| 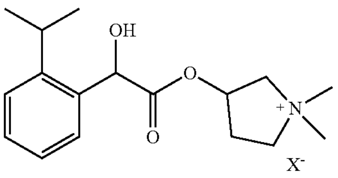 |
| 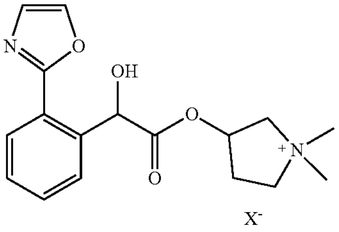 |
| 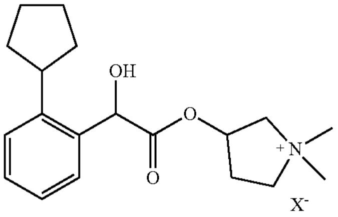 |
| 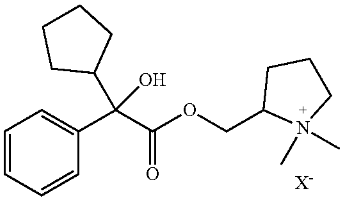 |

wherein $X^-$ is a pharmaceutically acceptable counterion.

In some embodiments, the present disclosure also provides a salt selected from those shown in Table 2 below:

TABLE 2

| List of Further Exemplary Salts of the Present Disclosure |
|---|
| 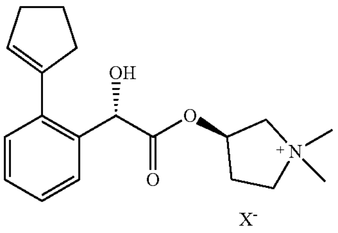 |
| 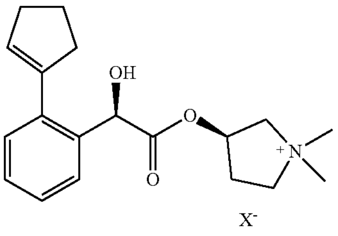 |

TABLE 2-continued

List of Further Exemplary Salts of the Present Disclosure

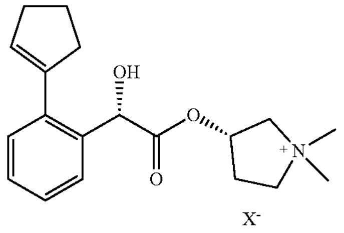

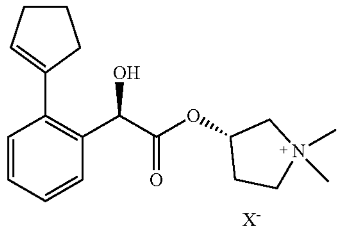

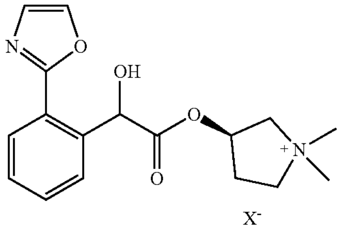

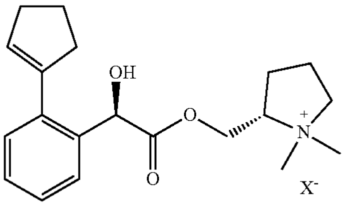

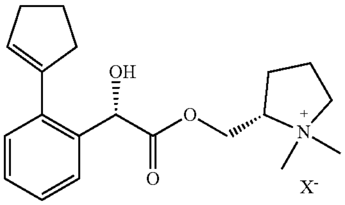

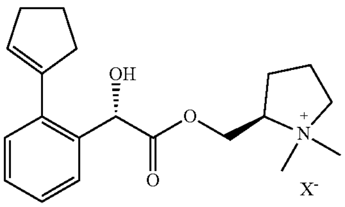

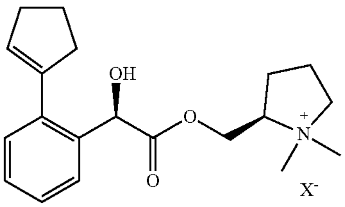

TABLE 2-continued

List of Further Exemplary Salts of the Present Disclosure

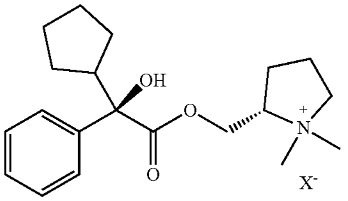

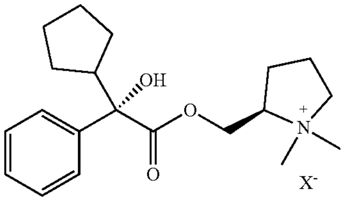

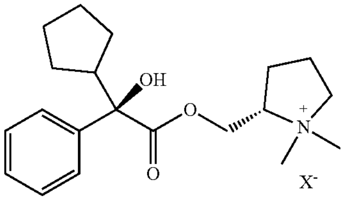

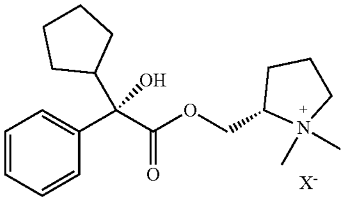

wherein $X^-$ is a pharmaceutically acceptable counterion.

In some embodiments, to the extent applicable, the genus of compounds described herein also excludes any specifically known compounds or salts prior to this disclosure. In some embodiments, to the extent applicable, any sub-genus of species of compounds or salts prior to this disclosure that are entirely within a genus of compounds described herein can also be excluded from the genus herein. For example, to the extent applicable, glycopyrrolate or its precursors is excluded from the genus of compounds/salts described herein related to Formula I or II.

Formula II

The salt of Formula I herein can be typically from reacting the corresponding amine having a Formula II:

Formula II

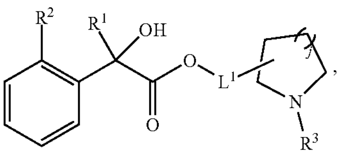

with a $R^4$ group donor, such as $R^4$-$Lg^1$, wherein $Lg^1$ is a leaving group, such as a halide (e.g., I), wherein the variables $L^1$, $R^1$, $R^2$, $R^3$, $R^4$, and j can have any of the respective definition described herein in connection with Formula I (including its subformulae) in any combination.

In some embodiments, the present disclosure also provides a compound of Formula II, or a salt thereof, Formula II

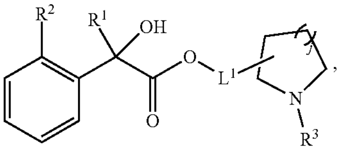

wherein:

$R^1$ is hydrogen or an optionally substituted $C_{3-8}$ carbocyclyl;

$L^1$ is null, $C_{1-4}$ alkylene, or $C_{1-4}$ heteroalkylene;

$R^2$ is hydrogen, $C_{1-6}$ alkyl, $C_{2-6}$ alkenyl, $C_{2-6}$ alkynyl, $C_{3-8}$ carbocyclyl, 4-8 membered heterocyclyl, phenyl, or 5-10 membered heteroaryl, each of which is optionally substituted;

$R^3$ is hydrogen or $C_{1-6}$ alkyl; and j is 0, 1 or 2.

In some embodiments, the compound of Formula II can have a formula according to Formula II-1:

Formula II-1

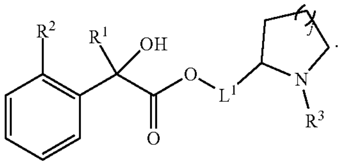

In some embodiments, the compound of Formula II can have a formula according to Formula II-2:

Formula II-2

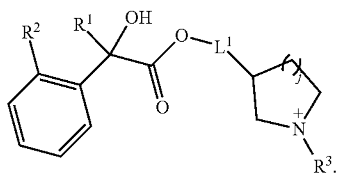

The definitions of $L^1$, $R^1$, $R^2$, $R^3$, and j in Formula II (e.g., Formula II-1 or II-2) include any of those respective definitions described herein in connection with Formula I (including its subformulae). For example, in some embodiments, $L^1$ in Formula II can be null. In some embodiments, $L^1$ in Formula II can be a $C_{1-4}$ alkylene such as $CH_2$. In some embodiments, $R^1$ in Formula II can be hydrogen. In some embodiments, $R^1$ in Formula II can be cyclopentyl. In some embodiments, $R^2$ in Formula II can be hydrogen. In some embodiments, $R^2$ in Formula II can be $C_{3-6}$ cycloalkyl, such as cyclopropyl, cyclobutyl, cyclopentyl, or cyclohexyl, which can be optionally substituted, e.g., as described herein. In some embodiments, $R^2$ in Formula II can be $C_{4-7}$ cycloalkenyl, such as cyclopentenyl, which can be optionally substituted, e.g., as described herein. In some embodiments, j in Formula II is 1. In some embodiments, $R^3$ in Formula II is methyl. Other suitable groups or definitions for $L^1$, $R^1$, $R^2$, $R^3$, and j in Formula II include any of those discussed herein in connection with Formula I (including its subformulae) in any combination.

In some embodiments, the compound of Formula II-2 can also be used to prepare a pharmaceutically acceptable salt, such as an acid addition salt or a quaternary salt such as those having Formula I.

Compounds of Formula II can be readily prepared by those skilled in the art in view of the present disclosure, which in turn can be used for the preparation of the salts of Formula I as discussed herein. Exemplary procedures are also shown in the Examples section.

For example, compounds of Formula II can be prepared by following Scheme A shown below. Thus, compound A can be coupled with compound B under an ester forming condition to provide compound C, which can then be converted into the compound of Formula II through deprotecting and optionally converting G into $R^2$. As would be apparent to those skilled in the art, the $R^2$ group can also be introduced earlier in the synthesis. Thus, in some embodiments, $R^2$ can also be the same as G group. In embodiments where G group is not the same as $R^2$, it is typically a leaving group such as a halide or a sulfonate containing leaving group (e.g., O-Ts, O-Ms, O-Tf), etc., which can react with a $R^2$ donor, such as under palladium catalyzed cross coupling condition. $Pg^1$ in compounds A and C is typically an oxygen protecting group, e.g., described herein. Suitable protecting groups for $Pg^1$ are not particularly limited. The definitions of $L^1$, $R^1$, $R^2$, $R^3$, and j in the compounds shown in Scheme A include any of those respective definitions described herein in connection with Formula II (including its subformulae) in any combination.

Scheme A

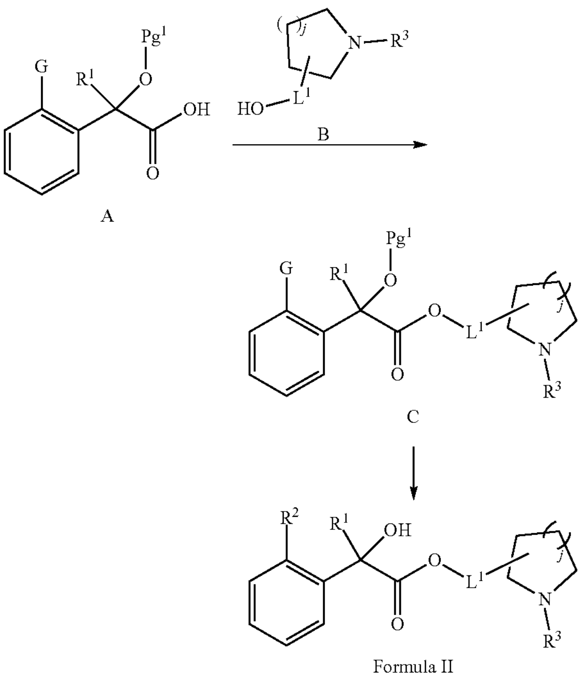

As will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in "Protective Groups in Organic Synthesis", $4^{th}$ ed. P. G. M. Wuts; T. W. Greene, John Wiley, 2007, and references cited therein. The reagents for the reactions described herein are generally known compounds or can be prepared by known procedures or obvious modifications thereof. For example, many of the reagents are available from commercial suppliers such as Aldrich Chemical Co. (Milwaukee, Wisconsin, USA), Sigma (St. Louis, Missouri, USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplemental (Elsevier Science Publishers, 1989), Organic Reactions, Volumes 1-40 (John Wiley and Sons, 1991), March's Advanced Organic Chemistry, (Wiley, $7^{th}$ Edition), and Larock's Comprehensive Organic Transformations (Wiley-VCH, 1999), and any of available updates as of this filing.

Pharmaceutical Compositions

Certain embodiments are directed to a pharmaceutical composition comprising one or more compounds/salts of the present disclosure.

The pharmaceutical composition can optionally contain a pharmaceutically acceptable excipient. In some embodiments, the pharmaceutical composition comprises a compound/salt of the present disclosure (e.g., a compound/salt of Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, or I-6), any of Examples 1-12, or any of the salts shown in Table 1 or 2 herein, or a pharmaceutically acceptable salt thereof) and a pharmaceutically acceptable excipient. Pharmaceutically acceptable excipients are known in the art. Non-limiting suitable excipients include, for example, encapsulating materials or additives such as antioxidants, binders, buffers, carriers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof. See also Remington's The Science and Practice of Pharmacy, 21st Edition, A. R. Gennaro (Lippincott, Williams & Wilkins, Baltimore, Md., 2005; incorporated herein by reference), which discloses various excipients used in formulating pharmaceutical compositions and known techniques for the preparation thereof.

The pharmaceutical composition can include any one or more of the compounds of the present disclosure. For example, in some embodiments, the pharmaceutical composition comprises a compound/salt of Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, or I-6), any of Examples 1-12, or any of the salts shown in Table 1 or 2 herein, or a pharmaceutically acceptable salt thereof, e.g., in a therapeutically effective amount for treating hyperhidrosis. In any of the embodiments described herein, the pharmaceutical composition can comprise a compound/salt selected from any of Examples 1-12, or any of the salts shown in Table 1 or 2 herein, or a pharmaceutically acceptable salt thereof.

The pharmaceutical composition herein can be formulated for delivery via any of the known routes of delivery, which include but not limited to administering orally, nasally, transdermally, pulmonary, inhalationally, buccally, sublingually, intraperintoneally, subcutaneously, intramuscularly, intravenously, rectally, intrapleurally, intrathecally or parenterally. For example, in some embodiments, the pharmaceutical composition herein can be formulated for topical delivery. In some embodiments, the pharmaceutical composition herein can be formulated for oral administration. In some embodiments, the pharmaceutical composition herein can be formulated for parenteral administration. In some embodiments, the pharmaceutical composition herein can be formulated for inhalation, such as an aerosol spray, dry powder, etc. In some embodiments, the pharmaceutical composition herein can be formulated as eye drops.

In some embodiments, the pharmaceutical composition can be formulated for oral administration. The oral formulations can be presented in discrete units, such as capsules, pills, cachets, lozenges, or tablets, each containing a predetermined amount of the active compound; as a powder or granules; as a solution or a suspension in an aqueous or non-aqueous liquid; or as an oil-in-water or water-in-oil emulsion. Excipients for the preparation of compositions for oral administration are known in the art. Non-limiting suitable excipients include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof.

In some embodiments, the pharmaceutical composition is formulated for parenteral administration (such as intravenous injection or infusion, subcutaneous or intramuscular injection). The parenteral formulations can be, for example, an aqueous solution, a suspension, or an emulsion. Excipients for the preparation of parenteral formulations are known in the art. Non-limiting suitable excipients include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof.

In some embodiments, the pharmaceutical composition can be formulated for topical administration. Topical formulations comprising one or more salts of the present disclosure can be prepared by mixing the one or more salts with a variety of carrier materials or pharmaceutically acceptable excipients. Excipients suitable for the preparation of topical formulations are known in the art. Some examples of suitable excipients include alcohols, aloe vera gel, allantoin, glycerin, vitamin A and E oils, mineral oil, PPG2, myristyl propionate lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The topical formulations can additionally optionally include: lubricating agents such as talc, magnesium stearate, and mineral oil; wetting agents; emulsifying and suspending agents; preserving agents such as methyl- and propylhydroxy-benzoates; sweetening agents; colorants; perfumes; and flavoring agents. When the excipient serves as a diluent, it can be a solid, semi-solid, or liquid, which acts as a vehicle, carrier or medium for the salts. In some embodiments, the topical formulations herein can be in the form of powders, suspensions, emulsions, solutions, syrups, alcoholic solutions, ointments, topical cleansers, cleansing creams, skin gels, skin lotions, mousses, roll-ons, aerosol or non-aerosol sprays in cream or gel formulations and soft gelatin capsules. In some embodiments, the pharmaceutical composition can be formulated in the form of a topical solution, cream, ointment, mousse, gel, lotion, or powder. In some embodiments, the pharmaceutical composition can include excipients such as water, propylene glycol, citric acid, sodium citrate, tromethamine, alcohol (e.g., ethanol), preservative, etc. For example, exemplary topical formulations comprising one or more salts of the present disclosure can be in the form of a topical solution, such as those having an aqueous vehicle, an alcoholic vehicle, an aqueous alcoholic vehicle, etc., such as those including one or more of the following excipients: water, propylene glycol, citric acid, sodium citrate, tromethamine, alcohol (e.g., ethanol), preservative, polymers and other excipients. In some embodiments, the topical solution can be formulated as a wipe, which can be contained in a pouch resistant to leakage, e.g., with an inner lining of linear low density polyethylene (LLDPE). Exemplary topical formulations comprising one or more salts of the present disclosure can be prepared similarly to the methods described in U.S. Pat. Nos. 6,433,003, 8,618,160, 9,744,105, 10,052,267, 8,859,610, 9,259,414, 10,004,717, 10,543,192, and 10,548,875.

Compounds/salts of the present disclosure can be used alone, in combination with each other, or in combination with one or more additional therapeutic agents. When used in combination with one or more additional therapeutic agents, compounds of the present disclosure or pharmaceutical compositions herein can be administered to the subject either concurrently or sequentially in any order with such additional therapeutic agents. In some embodiments, the pharmaceutical composition can comprise one or more compounds of the present disclosure and the one or more additional therapeutic agents in a single composition. In some embodiments, the pharmaceutical composition comprising one or more compounds of the present disclosure can be included in a kit which also comprises a separate pharmaceutical composition comprising the one or more additional therapeutic agents.

The pharmaceutical composition can include various amounts of the compounds of the present disclosure, depending on various factors such as the intended use and potency and selectivity of the compounds. In some embodiments, the pharmaceutical composition comprises a therapeutically effective amount of a compound/salt of the present disclosure, e.g., for treating hyperhidrosis. In some embodiments, the pharmaceutical composition comprises a therapeutically effective amount (e.g., for treating hyperhidrosis) of the compound/salt of the present disclosure and a pharmaceutically acceptable excipient. As used herein, a therapeutically effective amount of a compound/salt of the present disclosure is an amount effective to treat a disorder, condition or disease as described herein, such as hyperhidrosis, which can depend on the recipient of the treatment, the disorder, condition or disease being treated and the severity thereof, the composition containing the compound, the time of administration, the route of administration, the duration of treatment, the compound potency, its rate of clearance and whether or not another drug is co-administered.

Method of Treatment/Use

Compounds/salts of the present disclosure have various utilities. For example, compounds of the present disclosure can be used as therapeutic active substances for the treatment and/or prophylaxis of disorders, conditions or diseases that are associated with mAChR receptors such as $M_3$ receptor. Accordingly, some embodiments of the present disclosure are also directed to methods of using one or more compounds of the present disclosure or pharmaceutical compositions herein for treating or preventing a disorder, condition or disease that may be responsive to the antagonism of mAChRs such as $M_3$ receptor in a subject in need thereof, such as for treating hyperhidrosis in a subject in need thereof.

In some embodiments, the present disclosure provides a method of treating or preventing a disorder, condition or disease that may be responsive to the antagonism of $M_3$ in a subject in need thereof. In some embodiments, the method comprises administering to the subject an effective amount of a compound of the present disclosure (e.g., a compound/salt of Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, or I-6), any of Examples 1-12, or any of the salts shown in Table 1 or 2 herein, or a pharmaceutically acceptable salt thereof), or an effective amount of a pharmaceutical composition described herein. The disorder, condition or disease that may be responsive to the antagonism of $M_3$ can include any of those described herein and any of those known in the art, such as hyperhidrosis, chronic obstructive pulmonary disease (COPD), pupil dilation, abdominal pain, etc.

In some embodiments, the present disclosure provides a method of inhibiting the activity of mAChRs such as $M_3$ receptor in a subject or a biological sample. In some embodiments, the method comprises contacting the mAchRs such as $M_3$ receptor with an effective amount of a compound of the present disclosure (e.g., a compound/salt of Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, or I-6), any of Examples 1-12, or any of the salts shown in Table 1 or 2 herein, or a pharmaceutically acceptable salt thereof) or an effective amount of a pharmaceutical composition described herein.

Hyperhidrosis is a disorder characterized by excessive sweating, namely sweating in excess of that required for the regulation of body temperature, that occurs in up to 1% of the population, with women being the predominant group affected by this condition. The excessive sweating associated with hyperhidrosis can occur in the hands (palmar hyperhidrosis), in the armpits (axillary hyperhidrosis), or in the feet (plantar hyperhidrosis). Hyperhidrosis affects 8.8 million individuals in the United States alone, of whom 50.8% are estimated to have axillary hyperhidrosis and 25-34% have palmar or plantar hyperhidrosis. The underlying cause for primary hyperhidrosis, i.e., idiopathic hyperhidrosis, is not completely understood, but it is widely believed that an overactive sympathetic nervous system is involved, as it is known that sweating is generally under the control of the sympathetic nervous system. Secondary hyperhidrosis can be distinguished from primary hyperhidrosis as being due to a disorder of the thyroid or pituitary gland, diabetes mellitus, tumors, gout, menopause, or certain drugs.

Various anticholinergic agents have been described as being useful for treating hyperhidrosis, such as eucatropine derivatives, oxybutynin, propantheline, benztropine, and various glycopyrrolate formulations, see e.g., U.S. Pat. Nos. 4,720,494, 6,433,003, 8,618,160, 9,744,105, 10,052,267, 8,859,610, 9,259,414, 10,004,717, 10,543,192, and 10,548,875, and also the Prescribing Information for Qbrexza, revised June 2018. Compounds or salts of the present disclosure can have similar or better anticholinergic effects when compared with these agents and are also useful for treating hyperhidrosis, see e.g., the Examples section.

In some embodiments, the present disclosure provides a method of treating hyperhidrosis in a subject in need thereof. In some embodiments, the method comprises administering to the subject a therapeutically effective amount of a compound of the present disclosure (e.g., a compound/salt of Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, or I-6), any of Examples 1-12, or any of the salts shown in Table 1 or 2 herein, or a pharmaceutically acceptable salt thereof), or a therapeutically effective amount of a pharmaceutical composition described herein. For the treatment of hyperhidrosis, the administering is typically through the topical route. In some embodiments, the hyperhidrosis is a primary hyperhidrosis. In some embodiments, the hyperhidrosis is a secondary hyperhidrosis. In some embodiments, the hyperhidrosis is a primary axillary hyperhidrosis. In some embodiments, the hyperhidrosis is a primary palmar hyperhidrosis. In some embodiments, the hyperhidrosis is a primary plantar hyperhidrosis. Typically, the subject is an adult subject or pediatric patients 9 years or older.

The methods of treatment herein are not limited to hyperhidrosis. For example, in some embodiments, the present disclosure also provides a method of treating peptic ulcers that involve excessive stomach acid production in a subject in need thereof. In some embodiments, the method comprises administering to the subject an effective amount of a compound of the present disclosure (e.g., a compound/salt of Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, or I-6), any of Examples 1-12, or any of the salts shown in Table 1 or 2 herein, or a pharmaceutically acceptable salt thereof), or an effective amount of a pharmaceutical composition described herein.

In some embodiments, the present disclosure also provides a method of reducing drooling in a subject in need thereof, e.g., in children ages 3 to 16. In some embodiments, the method comprises administering to the subject an effective amount of a compound of the present disclosure (e.g., a compound/salt of Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, 1-4, I-4-E1, I-4-E2, I-4-E3, I-4-E4, I-5, or I-6), any of Examples 1-12, or any of the salts shown in Table 1 or 2 herein, or a pharmaceutically acceptable salt thereof), or an effective amount of a pharmaceutical composition described herein.

In some embodiments, the present disclosure also provides a method of reducing secretions in stomach or airway in a subject in need thereof. In some embodiments, the method comprises administering to the subject an effective amount of a compound of the present disclosure (e.g., a compound/salt of Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, or I-6), any of Examples 1-12, or any of the salts shown in Table 1 or 2 herein, or a pharmaceutically acceptable salt thereof), or an effective amount of a pharmaceutical composition described herein.

In some embodiments, the present disclosure also provides a method of protecting heart and nervous system in a subject in need thereof, e.g., patients under general anesthesia. In some embodiments, the method comprises administering to the subject an effective amount of a compound of the present disclosure (e.g., a compound/salt of Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, or I-6), any of Examples 1-12, or any of the salts shown in Table 1 or 2 herein, or a pharmaceutically acceptable salt thereof), or an effective amount of a pharmaceutical composition described herein.

In some embodiments, the present disclosure also provides a method of treating chronic obstructive pulmonary disease (COPD) in a subject in need thereof. In some embodiments, the method comprises administering to the subject a therapeutically effective amount of a compound of the present disclosure (e.g., a compound/salt of Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, or I-6), any of Examples 1-12, or any of the salts shown in Table 1 or 2 herein, or a pharmaceutically acceptable salt thereof), or an effective amount of a pharmaceutical composition described herein. In some embodiments, the method of treating COPD herein can include administering to the subject one or more additional therapeutic agents that are effective in treating COPD, which include any of those known in the art, such as bronchodilators, β-adrenergic agonists, anti-inflammatory agents including but not limited to inhaled steroids, oral steroids, Phosphodiesterase-4 inhibitors, JAK inhibitors, TYK2 inhibitors, NLRP3 inhibitors, PI3K inhibitors, SYK inhibitors, BTK inhibitors, IRAK1 and/or IRAK4 inhibitors, Theophylline, antibiotics, etc.

In some embodiments, the present disclosure also provides a method of inducing pupil dilation in a subject in need thereof. In some embodiments, the method comprises administering to the subject an effective amount of a compound of the present disclosure (e.g., a compound/salt of Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, or I-6), any of Examples 1-12, or any of the salts shown in Table 1 or 2 herein, or a pharmaceutically acceptable salt thereof), or an effective amount of a pharmaceutical composition described herein. Typically, the method of inducing pupil dilation comprises administering the compound of the present disclosure formulated as an eye drop.

In some embodiments, the present disclosure also provides a method of treating abdominal pain in a subject in need thereof. In some embodiments, the method comprises administering to the subject an effective amount of a compound of the present disclosure (e.g., a compound/salt of Formula I (e.g., Formula I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, or I-6), any of Examples 1-12, or any of the salts shown in Table 1 or 2 herein, or a pharmaceutically acceptable salt thereof), or an effective amount of a pharmaceutical composition described herein. Typically, the method of treating abdominal pain comprises orally administering the compound of the present disclosure.

The administering in the methods herein is not limited to any particular route of administration. For example, in some embodiments, the administering can be orally, nasally, topically, transdermally, pulmonary, inhalationally, buccally, sublingually, intraperintoneally, subcutaneously, intramuscularly, intravenously, rectally, intrapleurally, intrathecally and parenterally. In some embodiments, the administering is topically. In some embodiments, the administering is orally. In some embodiments, the administering is parenterally.

As discussed herein, compounds of the present disclosure can be used as a monotherapy or in a combination therapy. In some embodiments according to the methods described herein, compounds of the present disclosure can be administered as the only active ingredient(s). In some embodiments, one or more compounds of the present disclosure can be used in combination with an additional therapy, e.g., additional therapy that is effective in treating hyperhidrosis. In some embodiments according to the methods described herein, one or more compounds of the present disclosure can also be co-administered with an additional therapeutic agent, e.g., an agent that is effective in treating hyperhidrosis, either concurrently or sequentially in any order, to the subject in need thereof.

Dosing regimen including doses for the methods described herein can vary and be adjusted, which can depend on the recipient of the treatment, the disorder, condition or disease being treated and the severity thereof, the composition containing the compound, the time of administration, the route of administration, the duration of treatment, the compound potency, its rate of clearance and whether or not another drug is co-administered.

Definitions

It is meant to be understood that proper valences are maintained for all moieties and combinations thereof.

It is also meant to be understood that a specific embodiment of a variable moiety herein can be the same or different as another specific embodiment having the same identifier.

Suitable groups for use in compounds of Formula I and II, or subformula thereof, as applicable, are independently selected. The described embodiments of the present disclosure can be combined. Such combination is contemplated and within the scope of the present disclosure. For example, it is contemplated that the definition(s) of any one or more of $R^1$, $R^2$, $R^3$, $R^4$, $L^1$, $X^-$, and j of Formula I can be combined with the definition of any one or more of the other(s) of $R^1$, $R^2$, $R^3$, $R^4$, $L^1$, $X^-$, and j as applicable, and the resulted compounds from the combination are within the scope of the present disclosure. Combinations of other variables for other Formulae should be understood similarly.

The symbol,  whether utilized as a bond or displayed perpendicular to (or otherwise crossing) a bond, indicates the point at which the displayed moiety is attached to the remainder of the molecule. It should be noted that the immediately connected group or groups may be shown beyond the symbol, 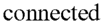, to indicate connectivity, as would be understood by those skilled in the art.

Definitions of specific functional groups and chemical terms are described in more detail below. The chemical elements are identified in accordance with the Periodic Table of the Elements, CAS version, *Handbook of Chemistry and Physics,* 75th Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry,* 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* 3rd Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high performance liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972). The disclosure additionally encompasses compounds described herein as individual isomers substantially free of other isomers, and alternatively, as mixtures of various isomers including racemic mixtures. When a stereochemistry is specifically drawn, unless otherwise contradictory from context, it should be understood that with respect to that particular chiral center(s) or axial chirality(ies), the compound can exist predominantly as the as-drawn stereoisomer, such as with less than 20%, less than 10%, less than 5%, less than 1%, by weight, by HPLC area, or both, or with a non-detectable amount of the other stereoisomer(s). The presence and/or amounts of stereoisomers can be determined by those skilled in the art in view of the present disclosure, including through the use of a chiral HPLC.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

As used herein, the term "compound(s) of the present disclosure" or as applicable, "salt(s) of the present disclosure", refers to any of the compounds/salts described herein according to Formula I (e.g., I-1, I-1-E1, I-1-E2, I-1-E3, I-1-E4, I-2, I-2-E1, I-2-E2, I-2-E3, I-2-E4, I-3, I-3-E1, I-3-E2, I-3-E3, I-3-E4, I-4, I-4-E1, I-4-E2, I-4-E3, I-4-E4, I-5, or I-6), Formula II (e.g., Formula II-1 or II-2), any of Examples 1-12, or any of the salts shown in Table 1 or 2 herein, isotopically labeled compound(s) thereof (such as a deuterated analog wherein one or more of the hydrogen atoms is substituted with a deuterium atom with an abundance above its natural abundance), possible regioisomers, possible stereoisomers thereof (including diastereoisomers, enantiomers, and racemic mixtures), tautomers thereof, conformational isomers thereof, and/or possible pharmaceutically acceptable salts thereof (e.g., acid addition salt such as HCl salt or base addition salt such as Na salt). Hydrates and solvates of the compounds of the present disclosure are considered compositions of the present disclosure, wherein the compound(s) is in association with water or solvent, respectively.

Compounds of the present disclosure can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to $^2H$, $^3H$, $^{13}C$ $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

As used herein, the phrase "administration" of a compound or salt, "administering" a compound or salt, or other variants thereof means providing the compound or salt or a prodrug of the compound or salt to the individual in need of treatment.

As used herein, the term "alkyl" as used by itself or as part of another group refers to a straight- or branched-chain aliphatic saturated hydrocarbon. In some embodiments, the alkyl can include one to twelve carbon atoms (i.e., $C_{1-12}$ alkyl) or the number of carbon atoms designated. In one embodiment, the alkyl group is a straight chain $C_{1-10}$ alkyl group. In another embodiment, the alkyl group is a branched chain $C_{3-10}$ alkyl group. In another embodiment, the alkyl group is a straight chain $C_{1-6}$ alkyl group. In another embodiment, the alkyl group is a branched chain $C_{3-6}$ alkyl group. In another embodiment, the alkyl group is a straight chain $C_{1-4}$ alkyl group. For example, a $C_{1-4}$ alkyl group includes methyl, ethyl, propyl (n-propyl), isopropyl, butyl (n-butyl), sec-butyl, tert-butyl, and iso-butyl. As used herein, the term "alkylene" as used by itself or as part of another group refers to a divalent radical derived from an alkyl group. For example, non-limiting straight chain alkylene groups include $—CH_2—CH_2—CH_2—CH_2—$, $—CH_2—CH_2—CH_2—$, $—CH_2—CH_2—$, and the like.

As used herein, the term "alkenyl" as used by itself or as part of another group refers to a straight- or branched-chain aliphatic hydrocarbon containing one or more, for example, one, two or three carbon-to-carbon double bonds. In one embodiment, the alkenyl group is a $C_{2-6}$ alkenyl group. In another embodiment, the alkenyl group is a $C_{2-4}$ alkenyl group. Non-limiting exemplary alkenyl groups include ethenyl, propenyl, isopropenyl, butenyl, sec-butenyl, pentenyl, and hexenyl.

As used herein, the term "alkynyl" as used by itself or as part of another group refers to a straight- or branched-chain aliphatic hydrocarbon containing one or more, for example, one to three carbon-to-carbon triple bonds. In one embodiment, the alkynyl has one carbon-carbon triple bond. In one embodiment, the alkynyl group is a $C_{2-6}$ alkynyl group. In another embodiment, the alkynyl group is a $C_{2-4}$ alkynyl group. Non-limiting exemplary alkynyl groups include ethynyl, propynyl, butynyl, 2-butynyl, pentynyl, and hexynyl groups.

As used herein, the term "alkoxy" as used by itself or as part of another group refers to a radical of the formula $OR^{a1}$, wherein $R^{a1}$ is an alkyl.

As used herein, the term "cycloalkoxy" as used by itself or as part of another group refers to a radical of the formula $OR^{a1}$, wherein $R^{a1}$ is a cycloalkyl.

As used herein, the term "haloalkyl" as used by itself or as part of another group refers to an alkyl substituted with one or more fluorine, chlorine, bromine and/or iodine atoms. In preferred embodiments, the haloalkyl is an alkyl group substituted with one, two, or three fluorine atoms. In one embodiment, the haloalkyl group is a $C_{1-10}$ haloalkyl group. In one embodiment, the haloalkyl group is a $C_{1-6}$ haloalkyl group. In one embodiment, the haloalkyl group is a $C_{1-4}$ haloalkyl group.

As used herein, the term "heteroalkyl," by itself or in combination with another term, means, unless otherwise stated, a stable straight or branched-chain alkyl group, e.g., having from 2 to 14 carbons, such as 2 to 10 carbons in the chain, one or more of the carbons has been replaced by a heteroatom selected from S, O, P and N, and wherein the nitrogen, phosphine, and sulfur atoms can optionally be oxidized and the nitrogen heteroatom can optionally be quaternized. The heteroatom(s) S, O, P and N may be placed at any interior position of the heteroalkyl group or at the position at which the alkyl group is attached to the remainder of the molecule. When the heteroalkyl is said to be substituted, the substituent(s) can replace one or more hydrogen atoms attached to the carbon atom(s) and/or the heteroatom(s) of the heteroalkyl. In some embodiments, the heteroalkyl is a $C_{1-4}$ heteroalkyl, which refers to the heteroalkyl defined herein having 1-4 carbon atoms. Examples of $C_{1-4}$ heteroalkyl include, but are not limited to, $C_4$ heteroalkyl such as $—CH_2—CH_2—N(CH_3)—CH_3$, $C_3$ heteroalkyl such as $—CH_2—CH_2—O—CH_3$, $—CH_2—CH_2—NH—CH_3$, $—CH_2—S—CH_2—CH_3$, $—CH_2—CH_2—S(O)—CH_3$, $—CH_2—CH_2—S(O)_2—CH_3$, $C_2$ heteroalkyl such as $—CH_2—CH_2—OH$, $—CH_2—CH_2—NH_2$, $—CH_2—NH(CH_3)$, $—O—CH_2—CH_3$ and $C_1$ heteroalkyl such as, $—CH_2—OH$, $—CH_2—NH_2$, $—O—CH_3$. Similarly, the term "heteroalkylene" by itself or as part of another substituent means a divalent radical derived from heteroalkyl, as exemplified, but not limited by, $—CH_2—CH_2—O—CH_2—CH_2—$ and $—O—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R or the like.

"Carbocyclyl" or "carbocyclic" as used by itself or as part of another group refers to a radical of a non-aromatic cyclic hydrocarbon group having at least 3 carbon atoms, e.g., from 3 to 10 ring carbon atoms ("$C_{3-10}$ carbocyclyl"), and zero heteroatoms in the non-aromatic ring system. The carbocyclyl group can be either monocyclic ("monocyclic carbocyclyl") or contain a fused, bridged or spiro ring system such as a bicyclic system ("bicyclic carbocyclyl") and can be saturated or can be partially unsaturated. Non-limiting exemplary carbocyclyl groups include cyclopropyl, cyclobutyl, cyclopentyl, cyclohexyl, cycloheptyl, cyclooctyl, norbornyl, decalin, adamantyl, cyclopentenyl, and cyclohexenyl. As used herein, the term "carbocyclylene" as used by itself or as part of another group refers to a divalent radical derived from the carbocyclyl group defined herein.

In some embodiments, "carbocyclyl" is fully saturated, which is also referred to as cycloalkyl. In some embodiments, the cycloalkyl can have from 3 to 10 ring carbon atoms ("$C_{3-10}$ cycloalkyl"). In preferred embodiments, the cycloalkyl is a monocyclic ring. As used herein, the term "cycloalkylene" as used by itself or as part of another group refers to a divalent radical derived from a cycloalkyl group, for example,

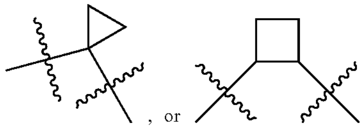

, or , etc.

"Heterocyclyl" or "heterocyclic" as used by itself or as part of another group refers to a radical of a 3-membered or larger, such as 3- to 14-membered, non-aromatic ring system having ring carbon atoms and at least one ring heteroatom, such as 1 to 4 ring heteroatoms, wherein each heteroatom is independently selected from nitrogen, oxygen, sulfur, boron, phosphorus, and silicon. In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings, the point of attachment can be on either ring. As used herein, the term "heterocyclylene" as used by itself or as part of another group refers to a divalent radical derived from the heterocyclyl group defined herein. The heterocyclyl or heterocylylene can be optionally linked to the rest of the molecule through a carbon or nitrogen atom.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" as used by itself or as part of another group refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{1-4}$ aryl"; e.g., anthracyl). As used herein, the term "arylene" as used by itself or as part of another group refers to a divalent radical derived from the aryl group defined herein.

"Aralkyl" as used by itself or as part of another group refers to an alkyl substituted with one or more aryl groups, preferably, substituted with one aryl group. Examples of aralkyl include benzyl, phenethyl, etc. When an aralkyl is said to be optionally substituted, either the alkyl portion or the aryl portion of the aralkyl can be optionally substituted.

"Heteroaryl" as used by itself or as part of another group refers to a radical of a 5-14 membered monocyclic, bicyclic, or tricyclic 4n+2 aromatic ring system (e.g., having 6 or 10 pi electrons shared in a cyclic array) having ring carbon atoms and at least one, preferably, 1-4, ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. Bicyclic heteroaryl groups wherein one ring does not contain a heteroatom (e.g., indolyl, quinolinyl, and the like) the point of attachment can be on either ring, i.e., either the ring bearing a heteroatom (e.g., 2-indolyl) or the ring that does not contain a heteroatom (e.g., 5-indolyl). As used herein, the term "heteroarylene" as used by itself or as part of another group refers to a divalent radical derived from the heteroaryl group defined herein.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" as used by itself or as part of another group refers to an alkyl substituted with one or more heteroaryl groups, preferably, substituted with one heteroaryl group. When a heteroaralkyl is said to be optionally substituted, either the alkyl portion or the heteroaryl portion of the heteroaralkyl can be optionally substituted.

An "optionally substituted" group, such as an optionally substituted alkyl, optionally substituted alkenyl, optionally substituted alkynyl, optionally substituted carbocyclyl, optionally substituted heterocyclyl, optionally substituted aryl, and optionally substituted heteroaryl groups, refers to the respective group that is unsubstituted or substituted. In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent can be the same or different at each position. Typically, when substituted, the optionally substituted groups herein can be substituted with 1-5 substituents. Substituents can be a carbon atom substituent, a nitrogen atom substituent, an oxygen atom substituent or a sulfur atom substituent, as applicable. Two of the optional substituents can join to form an optionally substituted ring structure, such as carbocyclyl (e.g., cycloalkyl), heterocyclyl, aryl, or heteroaryl ring. Substitution can occur on any available carbon, oxygen, or nitrogen atom, and can form a spirocycle. Typically, substitution herein does not result in an O—O, O—N, S—S, S—N (except $SO_2$—N bond), heteroatom-halogen, or —C(O)—S bond or three or more consecutive heteroatoms, with the exception of O—$SO_2$—O, O—$SO_2$—N, and N—$SO_2$—N, except that some of such bonds or connections may be allowed if in a stable aromatic system.

In a broad aspect, the permissible substituents herein include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a cycloalkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, an aryl, or a heteroaryl, each of which can be substituted, if appropriate.

Exemplary substituents include, but not limited to, alkyl, alkenyl, alkynyl, aryl, heteroaryl, -alkylene-aryl, -arylene-alkyl, -alkylene-heteroaryl, -alkenylene-heteroaryl, -alkynylene-heteroaryl, OH, hydroxyalkyl, haloalkyl, O-alkyl, O-haloalkyl, -alkylene-O-alkyl, O-aryl, O-alkylene-aryl, acyl, C(O)-aryl, halo, —$NO_2$, —CN, —$SF_5$, —C(O)OH, —C(O)O-alkyl, —C(O)O-aryl, —C(O)O-alkylene-aryl, —S(O)-alkyl, —$S(O)_2$-alkyl, —S(O)-aryl, —$S(O)_2$-aryl, —S(O)-heteroaryl, —$S(O)_2$-heteroaryl, —S-alkyl, —S-aryl, —S-heteroaryl, —S-alkylene-aryl, —S-alkylene-heteroaryl, —$S(O)_2$-alkylene-aryl, —$S(O)_2$-alkylene-heteroaryl, cycloalkyl, heterocycloalkyl, —O—C(O)-alkyl, —O—C(O)-aryl, —O—C(O)-cycloalkyl, —C(═N—CN)—$NH_2$, —C(═NH)—$NH_2$, —C(═NH)—NH(alkyl), —$N(Y_1)(Y_2)$, -alkylene-$N(Y_1)(Y_2)$, $C(O)N(Y_1)(Y_2)$ and —$S(O)_2N(Y_1)(Y_2)$, wherein $Y_1$ and $Y_2$ can be the same or different and are independently selected from the group consisting of hydrogen, alkyl, aryl, cycloalkyl, and -alkylene-aryl.

Some examples of suitable substituents include, but not limited to, ($C_1$-$C_8$)alkyl groups, ($C_2$-$C_8$)alkenyl groups, ($C_2$-$C_8$)alkynyl groups, ($C_3$-$C_{10}$)cycloalkyl groups, halogen (F, Cl, Br or I), halogenated ($C_1$-$C_8$)alkyl groups (for example but not limited to $CF_3$), —O—($C_1$-$C_8$)alkyl groups, —OH, —S—($C_1$-$C_8$)alkyl groups, —SH, —NH($C_1$-$C_8$)alkyl groups, —N(($C_1$-$C_8$)alkyl)$_2$ groups, —$NH_2$, C(O)$NH_2$, —C(O)NH($C_1$-$C_8$)alkyl groups, —C(O)N(($C_1$-$C_8$)alkyl)$_2$, —NHC(O)H, —NHC(O) ($C_1$-$C_8$)alkyl groups, NHC(O) ($C_3$-$C_8$)cycloalkyl groups, —N(($C_1$-$C_8$)alkyl)C(O)H, —N(($C_1$-$C_8$)alkyl)C(O)($C_1$-$C_8$)alkyl groups, —NHC(O)$NH_2$, —NHC(O)NH($C_1$-$C_8$)alkyl groups, —N(($C_1$-$C_8$)alkyl)C(O)$NH_2$ groups, —NHC(O)N(($C_1$-$C_8$)alkyl)$_2$ groups, —N(($C_1$-$C_8$)alkyl)C(O)N(($C_1$-$C_8$)alkyl)$_2$ groups, —N(($C_1$-$C_8$)alkyl)C(O)NH(($C_1$-$C_8$)alkyl), —C(O)H, —C(O)($C_1$-$C_8$) alkyl groups, —CN, —$NO_2$, —S(O)($C_1$-$C_8$)alkyl groups, —$S(O)_2$($C_1$-$C_8$)alkyl groups, —$S(O)_2$N(($C_1$-$C_8$)alkyl)$_2$ groups, —$S(O)_2$NH($C_1$-$C_8$)alkyl groups, —$S(O)_2$NH($C_3$-$C_8$)cycloalkyl groups, —$S(O)_2NH_2$ groups, —NHS$(O)_2$($C_1$-$C_8$)alkyl groups, —N(($C_1$-$C_8$)alkyl)S$(O)_2$($C_1$-$C_8$)alkyl groups, —($C_1$-$C_8$)alkyl-O—($C_1$-$C_8$)alkyl groups, —O—($C_1$-$C_5$)alkyl-O—($C_1$-$C_8$)alkyl groups, —C(O)OH, —C(O)O($C_1$-$C_8$)alkyl groups, NHOH, NHO($C_1$-$C_8$)alkyl groups, —O-halogenated ($C_1$-$C_8$)alkyl groups (for example but not limited to —$OCF_3$), —$S(O)_2$-halogenated ($C_1$-$C_8$)alkyl groups (for example but not limited to —$S(O)_2CF_3$), —S-halogenated ($C_1$-$C_8$)alkyl groups (for example but not limited to —$SCF_3$), —($C_1$-$C_6$) heterocycle (for example but not limited to pyrrolidine, tetrahydrofuran, pyran or morpholine), —($C_1$-$C_6$) heteroaryl (for example but not limited to tetrazole, imidazole, furan, pyrazine or pyrazole), -phenyl, —NHC(O)O—($C_1$-$C_6$)alkyl groups, —N(($C_1$-$C_6$)alkyl)C(O)O—($C_1$-$C_6$)alkyl groups, —C(═NH)—($C_1$-$C_6$)alkyl groups, —C(═NOH)—($C_1$-$C_6$)alkyl groups, or —C(═N—O—($C_1$-$C_6$)alkyl)-($C_1$-$C_6$)alkyl groups.

Exemplary carbon atom substituents include, but are not limited to, halogen, —CN, —$NO_2$, —$N_3$, hydroxyl, alkoxy, cycloalkoxy, aryloxy, amino, monoalkyl amino, dialkyl amino, amide, sulfonamide, thiol, acyl, carboxylic acid, ester, sulfone, sulfoxide, alkyl, haloalkyl, alkenyl, alkynyl, $C_{3-10}$ carbocyclyl, $C_{6-10}$ aryl, 3-10 membered heterocyclyl, 5-10 membered heteroaryl, etc. For example, exemplary carbon atom substituents can include F, Cl, —CN, —$SO_2H$, —$SO_3H$, —OH, —$OC_{1-6}$ alkyl, —$NH_2$, —N($C_{1-6}$ alkyl)$_2$, —NH($C_{1-6}$ alkyl), —SH, —$SC_{1-6}$ alkyl, —C(═O)($C_{1-6}$ alkyl), —$CO_2H$, —$CO_2$($C_{1-6}$ alkyl), —OC(═O)($C_{1-6}$ alkyl), —$OCO_2$($C_{1-6}$ alkyl), —C(═O)$NH_2$, —C(═O)N($C_{1-6}$ alkyl)$_2$, —OC(═O)NH($C_{1-6}$ alkyl), —NHC(═O)($C_{1-6}$ alkyl), —N($C_{1-6}$ alkyl)C(═O)($C_{1-6}$ alkyl), —NHC$O_2$($C_{1-6}$ alkyl), —NHC(═O)N($C_{1-6}$ alkyl)$_2$, —NHC(═O)NH($C_{1-6}$ alkyl), —NHC(═O)$NH_2$, —NHS$O_2$($C_{1-6}$ alkyl), —$SO_2$N($C_{1-6}$ alkyl)$_2$, —$SO_2$NH($C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, $C_{1-6}$ alkyl, $C_{1-6}$ haloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal substituents can be joined to form ═O.

Nitrogen atoms can be substituted or unsubstituted as valency permits, and include primary, secondary, tertiary, and quaternary nitrogen atoms. Exemplary nitrogen atom substituents include, but are not limited to, hydrogen, acyl groups, esters, sulfone, sulfoxide, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two substituent groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl can be further substituted as defined herein. In certain embodiments, the substituent present on a nitrogen atom is a nitrogen protecting group (also referred to as an amino protecting group). Nitrogen protecting groups are well known in the art and include those described in detail in *Protective Groups in Organic Synthesis*, T. W. Greene and P. G. M. Wuts, $3^{rd}$ edition, John Wiley & Sons, 1999, incorporated by reference herein. Exemplary nitrogen protecting groups include, but not limited to, those forming carbamates, such as Carbobenzyloxy (Cbz) group, p-Methoxybenzyl carbonyl (Moz or MeOZ) group, tert-Butyloxycarbonyl (BOC) group, Troc, 9-Fluorenylmethyloxycarbonyl (Fmoc) group, etc., those forming an amide, such as acetyl, benzoyl, etc., those forming a benzylic amine, such as benzyl, p-methoxybenzyl, 3,4-dimethoxybenzyl, etc., those forming a sulfonamide, such as tosyl, Nosyl, etc., and others such as p-methoxyphenyl.

Exemplary oxygen atom substituents include, but are not limited to, acyl groups, esters, sulfonates, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl can be further substituted as defined herein. In certain embodiments, the oxygen atom substituent present on an oxygen atom is an oxygen protecting group (also referred to as a hydroxyl protecting group). Oxygen protecting groups are well known in the art and include those described in detail in *Protective Groups in Organic Synthesis*, T. W. Greene and P. G. M. Wuts, $3^{rd}$ edition, John Wiley & Sons, 1999, incorporated herein by reference. Exemplary oxygen protecting groups include, but are not limited to, those forming alkyl ethers or substituted alkyl ethers, such as methyl, allyl, benzyl, substituted benzyls such as 4-methoxybenzyl, methoxylmethyl (MOM), benzyloxymethyl (BOM), 2-methoxyethoxymethyl (MEM), etc., those forming silyl ethers, such as trymethylsilyl (TMS), triethylsilyl (TES), triisopropylsilyl (TIPS), t-butyldimethylsilyl (TBDMS), etc., those forming acetals or ketals, such as tetrahydropyranyl (THP), those forming esters such as formate, acetate, chloroacetate, dichloroacetate, trichloroacetate, trifluoroacetate, methoxyacetate, etc., those forming carbonates or sulfonates such as methanesulfonate (mesylate), benzylsulfonate, and tosylate (Ts), etc.

Unless expressly stated to the contrary, combinations of substituents and/or variables are allowable only if such combinations are chemically allowed and result in a stable compound. A "stable" compound is a compound that can be prepared and isolated and whose structure and properties remain or can be caused to remain essentially unchanged for a period of time sufficient to allow use of the compound for the purposes described herein (e.g., therapeutic administration to a subject).

In some embodiments, the "optionally substituted" alkyl, alkylene, heteroalkyl, heteroalkylene, alkenyl, alkynyl, carbocyclic, carbocyclylene, cycloalkyl, cycloalkylene, alkoxy, cycloalkoxy, heterocyclyl, or heterocyclylene herein can each be independently unsubstituted or substituted with 1, 2, 3, or 4 substituents independently selected from F, Cl, —OH, protected hydroxyl, oxo (as applicable), $NH_2$, protected amino, $NH(C_{1-4}$ alkyl) or a protected derivative thereof, $N(C_{1-4}$ alkyl(($C_{1-4}$ alkyl), $C_{1-4}$ alkyl, $C_{2-4}$ alkenyl, $C_{2-4}$ alkynyl, $C_{1-4}$ alkoxy, $C_{3-6}$ cycloalkyl, $C_{3-6}$ cycloalkoxy, phenyl, 5 or 6 membered heteroaryl containing 1, 2, or 3 ring heteroatoms independently selected from O, S, and N, 3-7 membered heterocyclyl containing 1 or 2 ring heteroatoms independently selected from O, S, and N, wherein each of the alkyl, alkenyl, alkynyl, alkoxy, cycloalkyl, cycloalkoxy phenyl, heteroaryl, and heterocyclyl, is optionally substituted with 1, 2, or 3 substituents independently selected from F, —OH, oxo (as applicable), $C_{1-4}$ alkyl, fluoro-substituted $C_{1-4}$ alkyl (e.g., $CF_3$), $C_{1-4}$ alkoxy and fluoro-substituted $C_{1-4}$ alkoxy. In some embodiments, the "optionally substituted" aryl, arylene, heteroaryl or heteroarylene group herein can each be independently unsubstituted or substituted with 1, 2, 3, or 4 substituents independently selected from F, Cl, —OH, —CN, $NH_2$, protected amino, $NH(C_{1-4}$ alkyl) or a protected derivative thereof, $N(C_{1-4}$ alkyl(($C_{1-4}$ alkyl), —S(=O)($C_{1-4}$ alkyl), —$SO_2$($C_{1-4}$ alkyl), $C_{1-4}$ alkyl, $C_{2-4}$ alkenyl, $C_{2-4}$ alkynyl, $C_{1-4}$ alkoxy, $C_{3-6}$ cycloalkyl, $C_{3-6}$ cycloalkoxy, phenyl, 5 or 6 membered heteroaryl containing 1, 2 or 3 ring heteroatoms independently selected from O, S, and N, 3-7 membered heterocyclyl containing 1 or 2 ring heteroatoms independently selected from O, S, and N, wherein each of the alkyl, alkenyl, alkynyl, alkoxy, cycloalkyl, cycloalkoxy, phenyl, heteroaryl, and heterocyclyl, is optionally substituted with 1, 2, or 3 substituents independently selected from F, —OH, oxo (as applicable), $C_{1-4}$ alkyl, fluoro-substituted $C_{1-4}$ alkyl, $C_{1-4}$ alkoxy and fluoro-substituted $C_{1-4}$ alkoxy.

"Halo" or "halogen" refers to fluorine (fluoro, —F), chlorine (chloro, —Cl), bromine (bromo, —Br), or iodine (iodo, —I).

The term "leaving group" is given its ordinary meaning in the art of synthetic organic chemistry and refers to an atom or a group capable of being displaced by a nucleophile. See, for example, Smith, *March Advanced Organic Chemistry* 6th ed. (501-502). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art.

The term "tautomers" or "tautomeric" refers to two or more interconvertible compounds resulting from tautomerization. The exact ratio of the tautomers depends on several factors, including for example temperature, solvent, and pH. Tautomerizations are known to those skilled in the art. Exemplary tautomerizations include keto-to-enol, amide-to-imide, lactam-to-lactim, enamine-to-imine, and enamine-to-(a different enamine) tautomerizations.

The term "subject" (alternatively referred to herein as "patient") as used herein, refers to an animal, preferably a mammal, most preferably a human, who has been the object of treatment, observation or experiment.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound described herein to a subject in need of such treatment.

The term "effective amount" or "therapeutically effective amount" refers to that amount of a compound or combination of compounds as described herein that is sufficient to effect the intended application including, but not limited to, prophylaxis or treatment of diseases. A therapeutically effective amount may vary depending upon the intended application (in vitro or in vivo), or the subject and disease condition being treated (e.g., the weight, age and gender of the subject), the severity of the disease condition, the manner of administration, etc. which can readily be determined by one of ordinary skill in the art. The term also applies to a dose that will induce a particular response in target cells and/or tissues. The specific dose will vary depending on the particular compounds chosen, the dosing regimen to be followed, whether the compound is administered in combination with other compounds, timing of administration, the tissue to which it is administered, and the physical delivery system in which the compound is carried.

As used herein, the singular form "a" "an", and "the", includes plural references unless it is expressly stated or is unambiguously clear from the context that such is not intended.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Headings and subheadings are used for convenience and/or formal compliance only, do not limit the subject technology, and are not referred to in connection with the interpretation of the description of the subject technology. Features described under one heading or one subheading of the subject disclosure may be combined, in various embodiments, with features described under other headings or subheadings. Further it is not necessarily the case that all features under a single heading or a single subheading are used together in embodiments.

EXAMPLES

The various starting materials, intermediates, and compounds of the embodiments herein can be isolated and purified where appropriate using conventional techniques such as precipitation, filtration, crystallization, evaporation, distillation, and chromatography. Characterization of these compounds can be performed using conventional methods such as by melting point, mass spectrum, nuclear magnetic resonance, and various other spectroscopic analyses. Exemplary embodiments of steps for performing the synthesis of products described herein are described in greater detail infra.

Example 1. Synthesis of (3R)-3-(2-hydroxy-2-(2-(oxazol-2-yl)phenyl)acetoxy)-1,1-dimethylpyrrolidin-1-ium trifluoroacetate

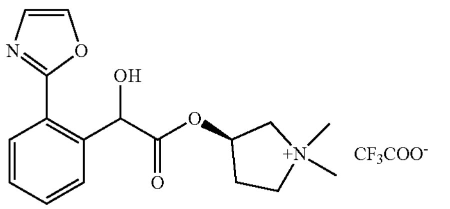

Scheme 1

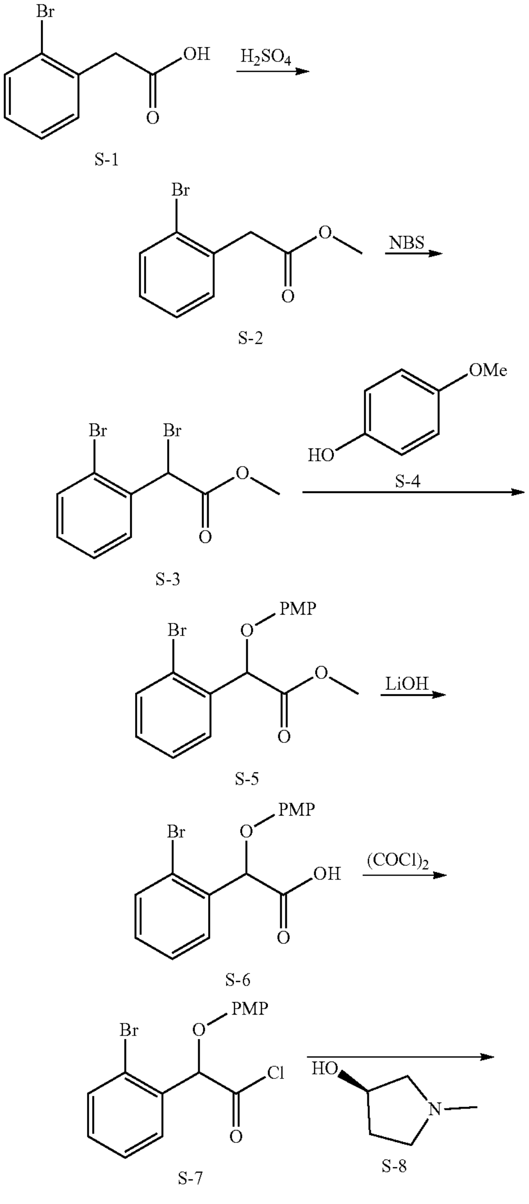

S-1

S-2

S-3

S-4

S-5

S-6

S-7

S-8

-continued

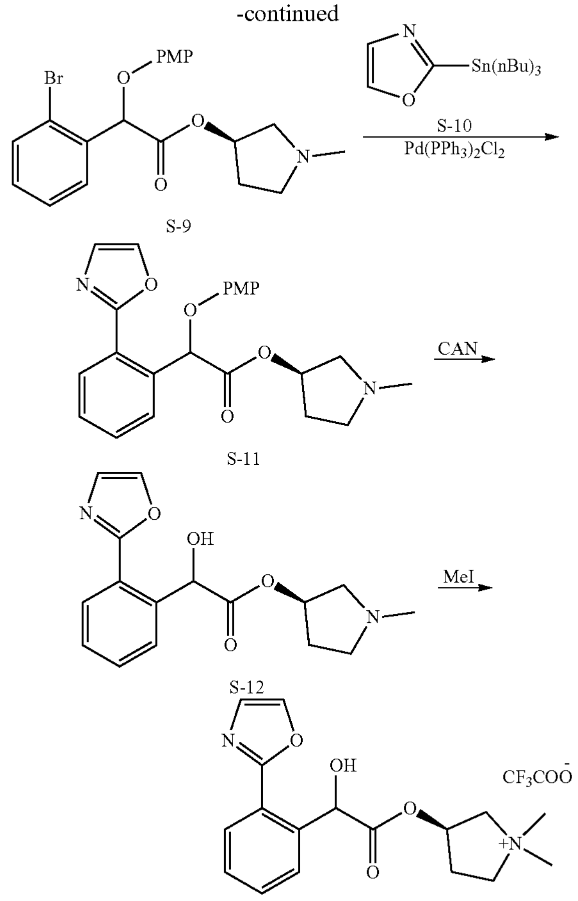

S-9

S-11

S-12

Example 1

Step 1. To a solution of 2-(2-bromophenyl)acetic acid (S-1) (10 g, 0.047 mol) in MeOH (100 mL) was added conc. $H_2SO_4$ (15.2 mL, 0.28 mol) dropwise. After addition, the resulting mixture was heated to reflux for 16 hrs. Solvent was evaporated and the residue was poured into ice water (100 mL). The mixture was extracted with EA (50 mL×2), dried and concentrated to give crude methyl 2-(2-bromophenyl)acetate (S-2). MS (ESI) m/z 229.1.

Step 2. A mixture of methyl 2-(2-bromophenyl)acetate (S-2) (10 g, crude, 0.0467 mol), NBS (9 g, 0.051 mol), and AIBN (3.83 g, 0.023 mol) in $CCl_4$ (100 mL) was heated at 80° C. for 16 hrs under $N_2$. Solvent was removed and the residue was diluted with DCM (150 mL), washed with water and brine, dried over $Na_2SO_4$ and concentrated to give methyl 2-bromo-2-(2-bromophenyl)acetate (S-3).

Step 3. To a solution of 4-methoxyphenol (S-4) (4.45 g, 0.0359 mol) in dry THE (250 mL) at 0° C. was added NaH (2.154 g, 0.054 mol) in small portions under $N_2$. The resulting mixture was stirred for 30 min at 0° C., followed by addition of methyl 2-bromo-2-(2-bromophenyl)acetate (S-3) (15 g, crude, 0.047 mol) and TBAI (776 mg, 0.007 mol). The resulting reaction mixture was stirred for additional 16 hr at rt. The reaction was quenched with aq. $NH_4Cl$ (100 mL) at 0° C., and then extracted with EA (50 mL×2). The combined organic phase was concentrated and the residue was purified by silica gel column chromatography (PE/EA=95:5 to 90:10) to give methyl 2-(2-bromophenyl)-2-(4-methoxyphenoxy)acetate (S-5). $^1$HNMR (400 MHz, CDCl3): 7.72-7.64 (m, 2H), 7.43-7.38 (m, 1H), 7.29-7.24 (m, 1H), 6.98-6.94 (m, 2H), 6.88-6.84 (m, 2H), 6.10 (s, 1H), 3.81 (s, 3H), 3.79 (s, 3H).

Step 4. To a solution of methyl 2-(2-bromophenyl)-2-(4-methoxyphenoxy)acetate (S-5) (1.0 g, 3.13 mmol) in MeOH (10 mL), THE (10 mL) and water (10 mL) was added LiOH (160 mg, 3.8 mmol), the resulting reaction mixture was stirred at 40° C. for 16 hrs. MeOH and THE was removed under vacuum and the residue was diluted with HCl (1N, 20 mL). It was extracted with EA (30 mL×3), dried and concentrated to give 2-(2-bromophenyl)-2-(4-methoxyphenoxy)acetic acid (S-6).

Step 5. To a solution of 2-(2-bromophenyl)-2-(4-methoxyphenoxy)acetic acid (S-6) (2.0 g, 5.931 mmol) in dry DCM (20 mL) was added $(COCl)_2$ (0.75 mL, 8.897 mmol) and DMF (one drop) at 0° C. The mixture was stirred at room temperature for 1 hour. And then the reaction mixture was concentrated in vacuum to give 2-(2-bromophenyl)-2-(4-methoxyphenoxy)acetyl chloride (S-7) (2.1 g, crude). The crude was used for next step and without further purification.

Step 6. To a solution of 2-(2-bromophenyl)-2-(4-methoxyphenoxy)acetyl chloride (S-7) (2.1 g, 5.91 mmol) in dry DCM (20 mL) at 0° C. was added (R)-1-methylpyrrolidin-3-ol (S-8) (717 mg, 7.09 mmol) and TEA (1.8 g, 17.73 mmol). The resulting reaction mixture was stirred at room temperature for 2 hrs. The reaction was quenched with water (30 mL) and extracted with DCM (30 mL×3). The combined organic layer was dried over $Na_2SO_4$ and filtered. The filtrate was concentrated and crude product was purified by silica-gel column chromatography eluting with MeOH: DCM (0-5%) to give (R)-1-methylpyrrolidin-3-yl 2-(2-bromophenyl)-2-(4-methoxyphenoxy)acetate (S-9). MS (ESI) m/z 422.1 $[M+H]^+$.

Step 7. A mixture of (R)-1-methylpyrrolidin-3-yl 2-(2-bromophenyl)-2-(4-methoxyphenoxy)acetate (S-9) (509 mg, 1.2 mmol), 2-(tributylstannyl)oxazole (S-10) (862 mg, 2.4 mmol), and $Pd(PPh_3)_4$ (277 mg, 0.24 mmol) in dioxane (15 mL) was heated at 100° C. for 16 h under $N_2$. Solvent was removed and the residue was purified by prep-TLC (DCM/MeOH=10:1) to give (R)-1-methylpyrrolidin-3-yl 2-(4-methoxyphenoxy)-2-(2-(oxazol-2-yl)phenyl)acetate (S-11). MS (ESI) m/z 409.4 $[M+H]^+$.

Step 8. To a solution of (R)-1-methylpyrrolidin-3-yl 2-(4-methoxyphenoxy)-2-(2-(oxazol-2-yl)phenyl)acetate (S-11) (80 mg, 0.2 mmol) in MeCN (15 mL) and water (15 mL) was added Cerium Ammonia Nitrate (CAN) (550 mg, 1.0 mmol). The resulting reaction mixture was stirred for 20 h at rt. Solvent was removed under vacuum and the residue was diluted with $H_2O$ and extracted with EA (15 mL×3). The combined organic phase was dried and concentrated. The residue was purified by prep-HPLC to give (R)-1-methylpyrrolidin-3-yl 2-hydroxy-2-(2-(oxazol-2-yl)phenyl)acetate (S-12).

Step 9. To a solution of (R)-1-methylpyrrolidin-3-yl 2-hydroxy-2-(2-(oxazol-2-yl)phenyl)acetate (S-12) (9 mg, 0.03 mmol) in 2-butanone (3 mL) was added $CH_3I$ (43 mg, 0.3 mol). The reaction mixture was loaded to seal tube and heated at 75° C. overnight. The reaction mixture was concentrated and the residue was purified by prep-HPLC to give (3R)-3-(2-hydroxy-2-(2-(oxazol-2-yl)phenyl)acetoxy)-1,1-dimethylpyrrolidin-1-ium trifluoroacetate (Example 1). $^1$H NMR (400 MHz, $D_2O$): 7.94-7.90 (m, 2H), 7.57-7.51 (m, 2H), 7.42-7.36 (m, 1H), 7.29-7.214 (m, 1H), 6.01-5.95 (m, 1H), 5.42 (br, 1H), 3.76-3.33 (m, 3H), 3.05 (s, 3H), 2.77-2.69 (m 3H), 2.66-2.51 (m, 2H), 2.17-2.08 (m, 1H), 1.89-1.79 (m, 1H). MS (ESI) m/z 317.1 $[M+H]^+$.

Example 2 and 3. Synthesis of (3R)-3-(2-(2-(cyclopent-1-en-1-yl)phenyl)-2-hydroxyacetoxy)-1,1-dimethylpyrrolidin-1-ium trifluoroacetate

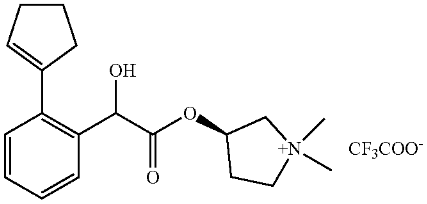

Scheme 2

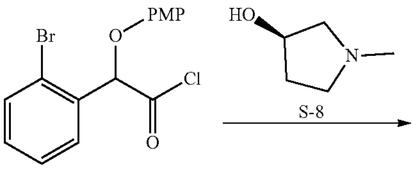

S-7

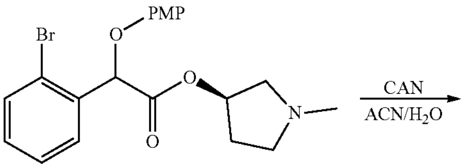

S-13

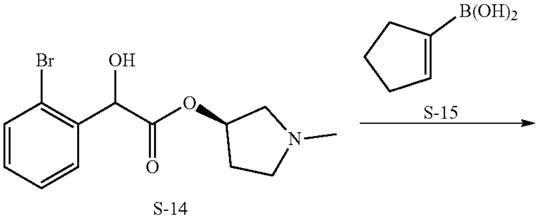

S-14

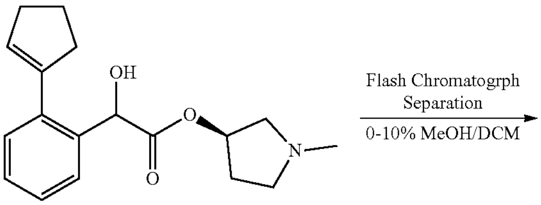

S-16

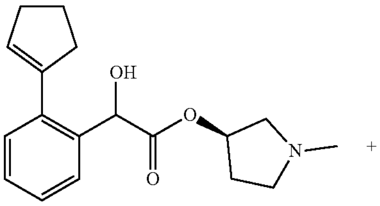

S-16a, Fast Isomer

-continued

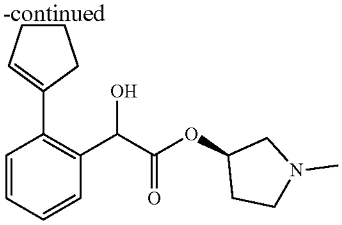

S-16b, Slow Isomer

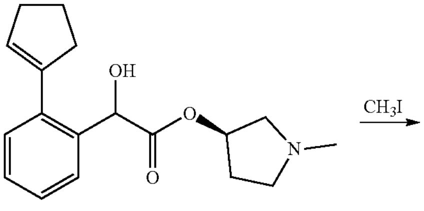

S-16a, Fast Isomer

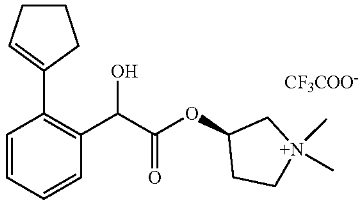

Example 2

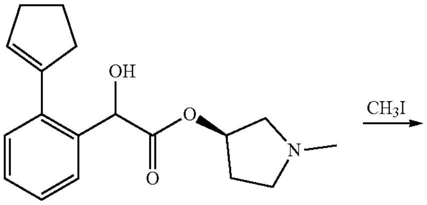

S-16b, Slow Isomer

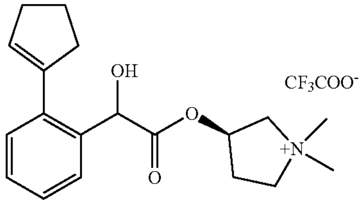

Example 3

Step 1. To a solution of 2-(2-bromophenyl)-2-(4-methoxyphenoxy)acetyl chloride (S-7) (2.1 g, 5.91 mmol) in dry DCM (20 mL) was added (R)-1-methylpyrrolidin-3-ol (S-8) (717 mg, 7.09 mmol) and TEA (1.8 g, 17.73 mmol) at ice bath. The mixture was stirred at room temperature for 2 hrs. The mixture was quenched with water (30 mL) and extracted with DCM (30 mL×3). The organic layer was dried over $Na_2SO_4$ and filtered. The filtrate was concentrated, and purified by silica-gel column chromatography eluting with MeOH:DCM (0-5%) to give (R)-1-methylpyrrolidin-3-yl 2-(2-bromophenyl)-2-(4-methoxyphenoxy)acetate (S-13). MS (ESI) m/z 422.1 $[M+H]^+$.

Step 2. To a solution of (R)-1-methylpyrrolidin-3-yl 2-(2-bromophenyl)-2-(4-methoxy phenoxy)acetate (S-13) (1.57 g, 3.74 mmol) in $CH_3CN/H_2O$ (30 mL/6 mL) was added CAN (6.14 g, 11.206 mmol). The mixture was stirred at room temperature overnight. The mixture was quenched with water (30 mL) and extracted with EA (30 mL×3). The organic layer was washed with HCl (0.5 M, 20 mL×2). The aqueous layer was basified with $Na_2CO_3$ aq to pH=9. The mixture was extracted with EA (30 mL×3). The combined organic layer was dried with $Na_2SO_4$ and filtered. The filtrate was concentrated to give (R)-1-methylpyrrolidin-3-yl 2-(2-bromophenyl)-2-hydroxy acetate (S-14) (600 mg, crude), which was used directly for next step without further purification. MS (ESI) m/z 316.0 $[M+H]^+$.

Step 3. A mixture of (R)-1-methylpyrrolidin-3-yl 2-(2-bromophenyl)-2-hydroxyacetate (S-14) (480 mg, 1.529 mmol), cyclopent-1-en-1-ylboronic acid (S-15) (257 mg, 2.293 mmol), $K_3PO_4$ (972 mg, 4.587 mmol) and Pd(dppf)$Cl_2$ (112 mg, 0.153 mmol) in 1,4-dioxane (15 mL) was heated to 110° C. for 16 hrs under nitrogen atmosphere. The mixture was quenched with water (30 mL) and extracted with EA (30 mL×3). The combined organic layer was dried with $Na_2SO_4$ and filtered. The filtrate was concentrated and purified by silica-gel column chromatography eluting with MeOH:DCM (0-10%) to give a mixture diastereomers of (R)-1-methylpyrrolidin-3-yl 2-(2-(cyclopent-1-en-1-yl)phenyl)-2-hydroxyacetate. This was further separated with column IH from Daicel, eluting with Hex-EtOH (9:1) to S-16a, the fast eluting isomer, and S-16b, the slow eluting isomer.

Step 4. To a solution of S-16a (70.0 mg, 0.233 mmol) in 2-butanone (3 mL) was added $CH_3I$ (3 drops). The mixture was stirred at 75° C. for 4 hrs. The mixture was concentrated and purified by prep-HPLC to give (R)-3-(−2-(2-(cyclopent-1-en-1-yl)phenyl)-2-hydroxyacetoxy)-1,1-dimethylpyrrolidin-1-ium trifluoroacetate (Example 2). $^1H$ NMR (400 MHz, $D_2O$): δ=7.47-7.39 (m, 4H), 5.89 (t, J=2.0 Hz, 1H), 5.71 (s, 1H), 5.57 (t, J=6 Hz, 1H), 3.89-3.77 (m, 2H), 3.61-3.48 (m, 2H), 3.20 (s, 3H), 2.93 (s, 3H), 2.79-2.75 (m, 1H), 2.72-2.68 (m, 2H), 2.58-2.54 (m, 2H), 2.19-2.11 (m, 1H), 2.08-2.00 (m, 2H). MS (ESI) m/z 316.2 $[M+H]^+$.

Example 3 was prepared from S-16b in the same way as Example 2. $^1H$ NMR (400 MHz, $D_2O$): δ=7.46-7.37 (m, 4H), 5.89 (t, J=2.0 Hz, 1H), 5.72 (s, 1H), 5.61 (br, 1H), 3.82-3.78 (dd, 1H), 3.71-3.57 (m, 2H), 3.53 (d, 1H), 3.16 (s, 3H), 2.81-2.75 (m, 1H), 2.76 (s, 3H), 2.73-2.68 (m, 2H), 2.59-2.55 (m, 2H), 2.42-2.34 (m, 1H), 2.05 (quint, 2H). MS (ESI) m/z 316.2 $[M+H]^+$.

Example 4 and 5. Synthesis of (3S)-3-(2-(2-(cyclopent-1-en-1-yl)phenyl)-2-hydroxyacetoxy)-1,1-dimethylpyrrolidin-1-ium trifluoroacetate

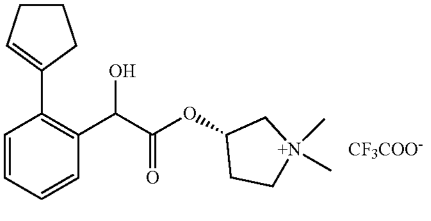

Example 4, 5 were synthesized starting from (S)-1-methylpyrrolidin-3-ol in the same way as described for Example 2, 3, with Example 4 derived from the fast eluting isomer of (S)-1-methylpyrrolidin-3-yl 2-(2-(cyclopent-1-en-1-yl)phenyl)-2-hydroxyacetate, and Example 5 from the corresponding slow eluting isomer. H NMR of Example 4 appears the same as Example 3, and $^1H$ NMR of Example 5 appears the same as Example 2.

Example 6 and 7. The synthesis of (R)-2-((2-(2-(cyclopent-1-en-1-yl)phenyl)-2-hydroxyacetoxy)methyl)-1,1-dimethylpyrrolidin-1-ium trifluoroacetate

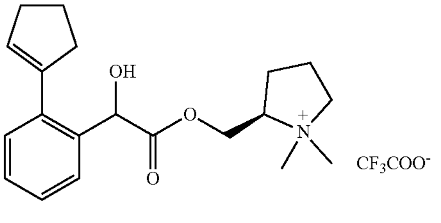

Scheme 3

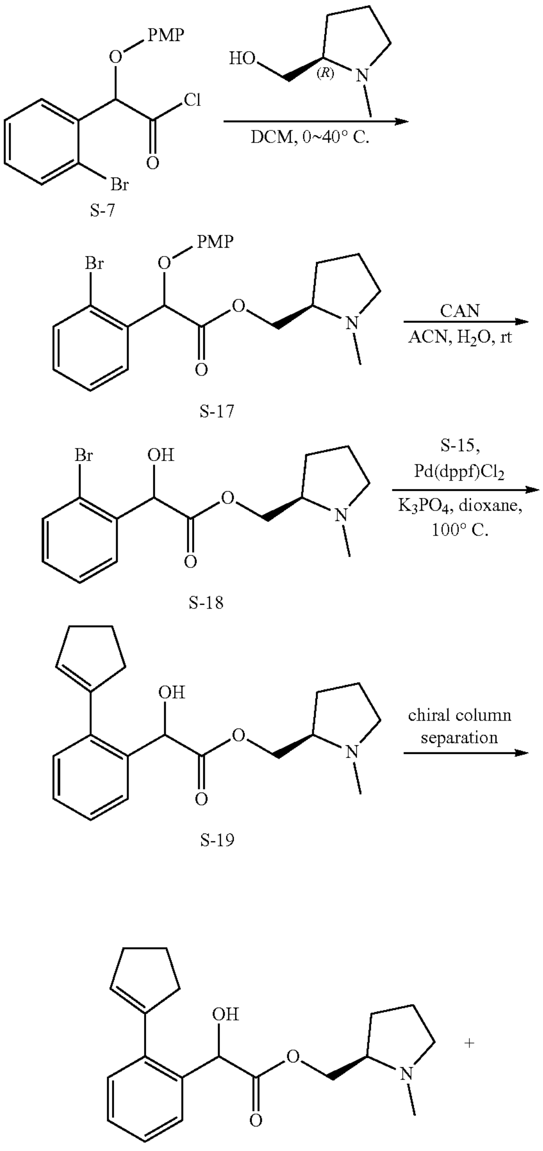

S-7

S-17

S-18

S-19

S-19a, fast isomer

-continued

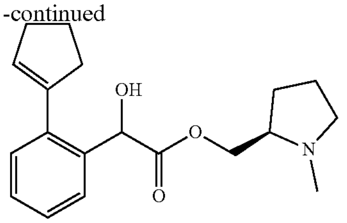

S-19b, slow isomer

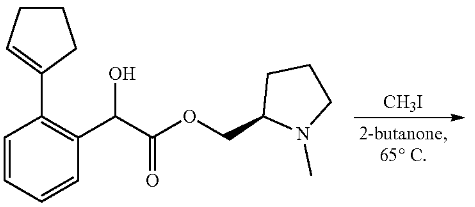

S-19a, fast isomer

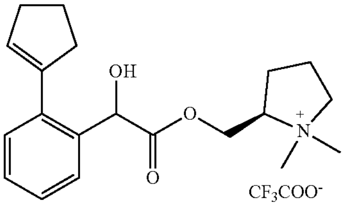

Example 6

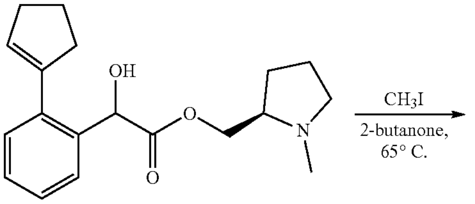

S-19b, slow isomer

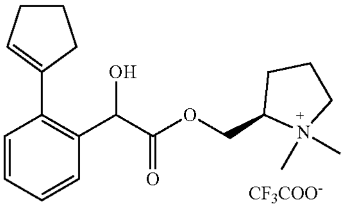

Example 7

Step 1. To a solution of (R)-(1-methylpyrrolidin-2-yl) methanol (0.68 g, 5.9 mmol) and TEA (1.19 g, 11.8 mmol) in DCM (20 mL) was added 2-(2-bromophenyl)-2-(4-methoxyphenoxy)acetyl chloride (S-7) (2.1 g, 5.9 mmol) in DCM (10 mL) at 0° C. over 20 min. The resulting reaction mixture was stirred at 45° C. for 2 h. The mixture was quenched with $H_2O$ and extracted with DCM. The combined organic phase was dried with $Na_2SO_4$ and concentrated to give the crude product. The crude product was purified by column chromatography on silica gel (PE/EA=1/1) to afford ((R)-1-methylpyrrolidin-2-yl)methyl 2-(2-bromophenyl)-2-(4-methoxyphenoxy)acetate (5-17). MS (ESI) m/z 433.9 $[M+H]^+$.

Step 2. To a solution of ((R)-1-methylpyrrolidin-2-yl) methyl 2-(2-bromophenyl)-2-(4-methoxyphenoxy)acetate (S-17) (2.1 g, 4.9 mmol) in $CH_3CN/H_2O$ (10 mL/10 mL) was added CAN (8.0 g, 14.6 mmol). The resulting reaction mixture was stirred at room temperature overnight. The mixture was concentrated and the residue was diluted with water (50 mL), extracted with EA (50 mL). The aqueous was adjusted to pH=9 using $Na_2CO_3$ solution. The resulting mixture was extracted with EA (100 mL×2). The combined organic phases were washed with brine, dried with $Na_2SO_4$, and concentrated to give crude ((R)-1-methylpyrrolidin-2-yl)methyl 2-(2-bromophenyl)-2-hydroxyacetate (S-18) (0.9 g, yield: 56.6%), which was used to next step directly without further purification. MS (ESI) m/z 327.9 $[M+H]^+$.

Step 3. A mixture of ((R)-1-methylpyrrolidin-2-yl)methyl 2-(2-bromophenyl)-2-hydroxyacetate (S-18) (0.8 g, 2.4 mmol), cyclopent-1-en-1-ylboronic acid (S-15) (0.4 g, 3.6 mmol), $K_3PO_4$ (1.01 g, 4.8 mmol) and $Pd(dppf)Cl_2$ (0.18 g, 0.24 mmol) in dioxane/$H_2O$ (10 mL/1 mL) was stirred at 100° C. under $N_2$ overnight. The reaction mixture was diluted with water (20 mL) and extracted with EA (50 mL). The organic phase was washed with brine, dried with $Na_2SO_4$, and concentrated. The residue was purified by prep-HPLC to give a diastereomeric mixture of ((R)-1-methylpyrrolidin-2-yl)methyl 2-(2-(cyclopent-1-en-1-yl) phenyl)-2-hydroxyacetate (S-19) (0.25 g, yield: 32.5%) as a brown oil. Further separation on a chiral column IH from Daicel, eluting with Hexane:EtOH (9:1, containing 0.3% of DEA) afforded S-19a as the fast isomer, and S-19b as the slow isomer.

Step 4. To a solution of S-19a (30 mg, 0.095 mmol) in 2-butanone (1 mL) was added $CH_3I$ (1 mL). The resulting reaction mixture was loaded to seal tube and stirred at 65° C. for 2 h. The mixture was concentrated and purified by prep-HPLC (0.1% TFA as additive), to afford Example 6, one enantiomer of (R)-2-((2-(2-(cyclopent-1-en-1-yl)phenyl)-2-hydroxyacetoxy)methyl)-1,1-dimethylpyrrolidin-1-ium trifluoroacetate. $^1H$ NMR (400 MHz, $D_2O$): 7.36-7.26 (m, 4H) 5.79-5.78 (t, J=2.2 Hz, 1H), 5.63 (s, 1H), 4.68-4.64 (m, 1H), 4.28-4.22 (m, 1H), 3.74-3.67 (m, 1H), 3.36-3.28 (m, 2H), 2.70 (s, 3H), 2.67 (s, 3H), 2.64-2.58 (m, 2H), 2.51-2.44 (m, 2H), 2.26-2.20 (m, 1H), 2.07-1.82 (m, 5H). MS (ESI) m/z 330.2 $[M+H]^+$.

Example 7 was prepared from S-19b, $^1H$ NMR (400 MHz, $D_2O$). 7.38-7.31 (m, 4H) 5.80-5.79 (t, J=2.0 Hz, 1H), 5.65 (s, 1H), 4.50-4.38 (m, 2H), 3.85-3.81 (m, 1H), 3.41-3.37 (m, 2H), 2.69 (s, 3H), 2.63-2.58 (m, 5H), 2.51-2.46 (m, 2H), 2.24-2.22 (m, 1H), 2.04-1.83 (m, 4H), 1.71-1.66 (m, 1H). MS (ESI) m/z 330.2 $[M+H]^+$.

Example 8 and 9. The synthesis of (S)-2-((2-(2-(cyclopent-1-en-1-yl)phenyl)-2-hydroxyacetoxy) methyl)-1,1-dimethylpyrrolidin-1-ium trifluoroacetate

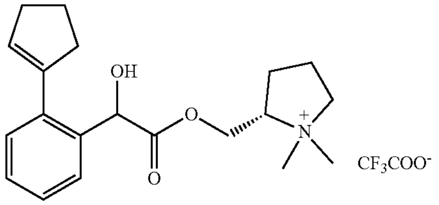

Example 8 and 9 were synthesized starting from (S)-(1-methylpyrrolidin-2-yl)methanol in the same way as described for Example 6 and 7, with Example 8 derived from the fast eluting isomer of ((S)-1-methylpyrrolidin-2-yl)methyl 2-(2-(cyclopent-1-en-1-yl)phenyl)-2-hydroxyacetate, and Example 9 from the corresponding slow eluting isomer. $^1$H NMR of Example 8 appears the same as Example 6, and $^1$H NMR of Example 9 appears the same as Example 7.

Example 10. Synthesis of 3-[2-(2-Cyclopentyl-phenyl)-2-hydroxy-acetoxy]-1,1-dimethyl-pyrrolidinium chloride Example 10

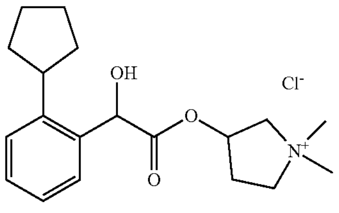

Scheme 4

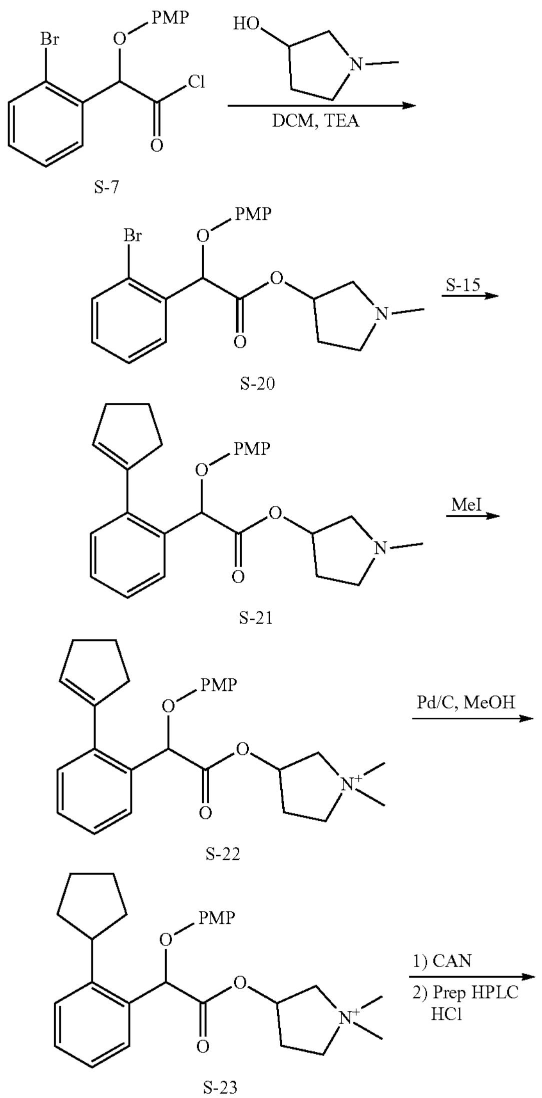

S-7

S-20

S-21

S-22

S-23

-continued

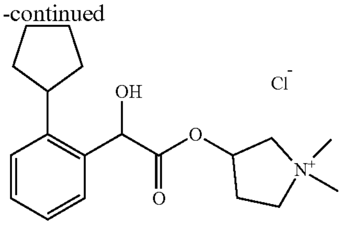

Example 10

Step 1. To a solution of 1-methylpyrrolidin-3-ol (300 mg, 2.97 mmol) and TEA (400 mg, 3.95 mmol) in DCM (15 mL) was added 2-(2-bromophenyl)-2-(4-methoxyphenoxy)acetyl chloride (S-7) (710 mg, 1.98 mmol) at 0° C. over 10 min. The mixture was stirred at room temperature for 2 hrs. The mixture was quenched with $H_2O$ and extracted with DCM. The combined organic phase was dried with $Na_2SO_4$ and concentrated to give the crude product. The crude product was purified by column chromatography on silica gel (PE/EA=1/1) to afford 1-methylpyrrolidin-3-yl 2-(2-bromophenyl)-2-(4-methoxyphenoxy)acetate (S-20). MS (ESI) m/z 422.1 $[M+H]^+$.

Step 2. To a mixture of 1-methylpyrrolidin-3-yl 2-(2-bromophenyl)-2-(4-methoxyphenoxy)acetate (S-20) (710 mg, 1.69 mmol) in dioxane/$H_2O$ (25 mL/5 mL) was added cyclopent-1-en-1-ylboronic acid (S-5) (491 mg, 2.53 mmol), $K_2CO_3$ (699 mg, 5.07 mmol) and Pd(dppf)$Cl_2$ (123 mg, 0.169 mmol). The resulting mixture was degassed and filled with $N_2$. The reaction mixture was then stirred at 110° C. overnight. The reaction mixture was diluted with water (20 mL) and extracted with EA (50 mL). The organic phase was washed with brine, dried with $Na_2SO_4$, and concentrated. The residue was purified by column chromatography on silica gel (DCM/MeOH=20/1) to afford 1-methylpyrrolidin-3-yl (2-cyclopent-1-enylphenyl)-(4-methoxyphenoxy)acetate (S-21). MS (ESI) m/z 408.2 $[M+H]^+$.

Step 3. To a solution of 1-methylpyrrolidin-3-yl (2-cyclopent-1-enylphenyl)-(4-methoxyphenoxy)acetate (S-21) (330 mg, 0.81 mmol) in 2-butanone (5 mL) was added $K_2CO_3$ (20 mg, 0.081 mmol) and $CH_3I$ (571 mg, 4.05 mmol). The resulting reaction mixture was loaded to seal tube and stirred at 75° C. overnight. The mixture was concentrated and purified by prep-HPLC to afford 3-[2-(2-cyclopent-1-enylphenyl)-2-(4-methoxyphenoxy)acetoxy]-1,1-dimethyl-pyrrolidinium trifluoroacetate (S-22). MS (ESI) m/z 422.3 $[M]^+$.

Step 4. A mixture of 3-[2-(2-cyclopent-1-enyl-phenyl)-2-(4-methoxy-phenoxy)-acetoxy]-1,1-dimethyl-pyrrolidinium trifluoroacetate (S-22) (81 mg, 0.189 mmol) and Pd/C (~20 mg, 20% wt.) in MeOH (10 mL) was degassed and filled with hydrogen using a balloon. The resulting mixture was then hydrogenated at r.t. for 16 hrs. The reaction mixture was filtered over celite and concentrated to give a crude 3-[2-(2-cyclopentyl-phenyl)-2-(4-methoxy-phenoxy)-acetoxy]-1,1-dimethyl-pyrrolidinium trifluoroacetate (S-23) which was directly used in the next step. MS (ESI) m/z 424.3 $[M]^+$.

Step 5. To a mixture of crude 3-[2-(2-cyclopentyl-phenyl)-2-(4-methoxy-phenoxy)-acetoxy]-1,1-dimethyl-pyrrolidinium trifluoroacetate (S-23) (80 mg, 0.189 mmol) in $CH_3CN/H_2O$ (5 mL/5 mL) was added CAN (625 mg, 1.14 mmol) in 2 portions at r.t. The resulting reaction mixture was stirred at room temperature overnight. The mixture was concentrated and the residue was diluted with water (10 mL) and extracted with EA (10 mL×2). The aqueous was adjusted to pH=9 using $Na_2CO_3$ solution and extracted with EA (10 mL×2) again. The combined organic phases were dried with $Na_2SO_4$ and concentrated. The residue was purified by prep-HPLC (0.1% TFA as additive), and product was treated with a few drops of HCl and lyophilized to give 3-[2-(2-Cyclopentyl-phenyl)-2-hydroxy-acetoxy]-1,1-dimethyl-pyrrolidinium chloride (Example 10). $^1H$ NMR (400 MHz, D2O, mixture of two diastereomers): 7.44-7.42 (m, 2H, both diastereomers), 7.36-7.33 (m, 2H, both diastereomers), 7.27-7.20 (m, 2H, both diastereomers), 5.72 (s, 1H, diastereomer 1), 5.70 (s, 1H, diastereomer 2), 5.54 (br, 2H, both diastereomers), 3.81-3.68 (m, 3H, both diastereomers), 3.63-3.41 (m, 5H, both diastereomers), 3.12 (s, 3H, diastereomer 1), 3.08 (3, 3H, diastereomer 2), 2.86 (s, 3H, diastereomer 1), 2.73-2.64 (m, 5H, both diastereomers), 2.32-2.29 (m, 1H, diastereomer 1), 2.08-1.92 (m, 5H, both diastereomers), 1.77-1.51 (m, 12H, both diastereomers). MS (ESI) m/z 318.2 $[M]^+$.

Example 11. Synthesis of 3-(2-([1,1'-biphenyl]-2-yl)-2-hydroxyacetoxy)-1,1-dimethylpyrrolidin-1-ium chloride Example 11

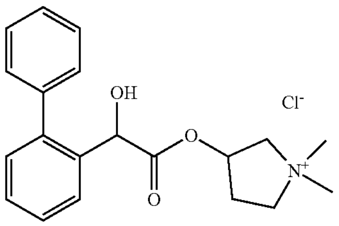

Scheme 5

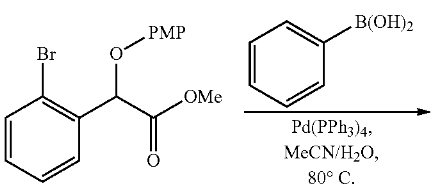

S-5

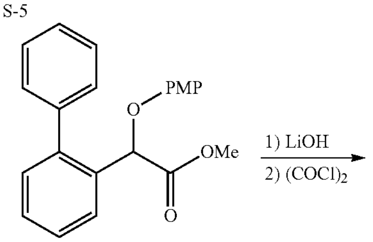

S-24

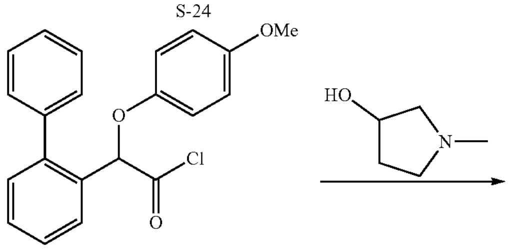

S-25

-continued

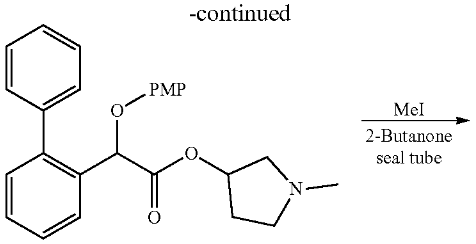

S-26

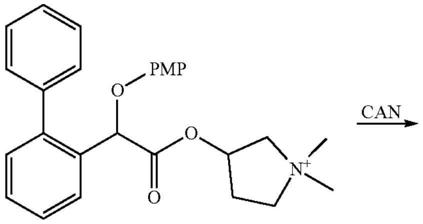

S-27

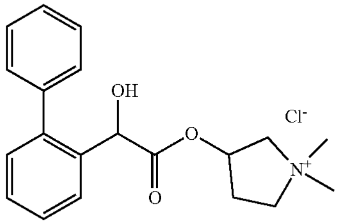

Example 11

Step 1. A mixture of methyl 2-(2-bromophenyl)-2-(4-methoxyphenoxy)acetate (S-5) (1.06 g, 3.02 mmol), phenylboronic acid (553 mg, 4.53 mmol), KOAc (444 mg, 4.53 mmol) and $Pd(PPh_3)_4$ (175 mg, 0.15 mmol) in $CH_3CN/H_2O$ (75 mL/16 mL) was degassed and filled with $N_2$. The resulting mixture was then heated at 80° C. overnight. The reaction mixture was concentrated and the residue was purified by column chromatography on silica gel (PE/EA=10/1) to provide methyl 2-([1,1'-biphenyl]-2-yl)-2-(4-methoxyphenoxy)acetate (S-24). MS (ESI) m/z 366.2 [M+18]+

Step 2. To a solution of methyl 2-([1,1'-biphenyl]-2-yl)-2-(4-methoxyphenoxy)acetate (S-24) (908 mg, 2.6 mmol) in MeOH/THF/$H_2O$ (10 mL/10 mL/10 mL) was added LiOH·$H_2O$ (131 mg, 3.12 mmol). The resulting mixture was stirred at 40° C. overnight. The reaction mixture was concentrated. The residue was diluted with water (10 mL), acidified with diluted HCl until pH reached 2 and extracted with EA (20 mL×3). The combined organic phase was washed with brine (20 mL), dried over $Na_2SO_4$, and concentrated to give 2-([1,1'-biphenyl]-2-yl)-2-(4-methoxyphenoxy)acetic acid. MS (ESI) m/z 333.2 $[M-H]^-$.

Step 3. To a mixture of 2-([1,1'-biphenyl]-2-yl)-2-(4-methoxyphenoxy)acetic acid (890 mg, 2.6 mmol) in DCM (15 mL) was added DMF (one drop) and oxalyl dichloride (500 mg, 3.9 mmol) at 0° C. dropwise. The mixture was stirred at r.t. for 2 h. The mixture was then concentrated to give biphenyl-2-yl-(4-methoxy-phenoxy)-acetyl chloride (S-25), which was directly used in the next step.

Step 4. To a mixture of 1-methylpyrrolidin-3-ol (240 mg, 2.36 mmol) and TEA (290 mg, 2.83 mmol) in DCM (20 mL) at 0° C. was added a mixture of 2-([1,1'-biphenyl]-2-yl)-2-(4-methoxyphenoxy)acetyl chloride (S-25) (900 mg, 2.60 mmol) in DCM (10 mL) dropwise during 20 min. After addition, the mixture was stirred for additional 2 hrs, left the temperature slowly warm to r.t. LCMS indicated the completion of reaction. The mixture was quenched with water and was extracted with DCM (30 mL×3). The combined organic phase was dried over $Na_2SO_4$ and concentrated. The residue was purified by column chromatography on silica gel (DCM/MeOH=20/1) to give 1-methylpyrrolidin-3-yl 2-([1,1'-biphenyl]-2-yl)-2-(4-methoxyphenoxy)acetate (S-26). MS (ESI) m/z 418.2 $[M+H]^+$.

Step 5. A pressure tube charged with 1-methylpyrrolidin-3-yl 2-([1,1'-biphenyl]-2-yl)-2-(4-methoxyphenoxy)acetate (S-26) (840 mg, 1.85 mmol) and Mel (1.15 mL, 18.5 mmol) in 2-butanone (10 mL) was sealed and heated at 75° C. for 16 h. The cooled reaction mixture was concentrated and the residue was purified by prep-HPLC (0.1% TFA as additive), the product fraction was treated with HCl and lyophilized to give 3-(2-([1,1'-biphenyl]-2-yl)-2-hydroxyacetoxy)-1,1-dimethylpyrrolidin-1-ium chloride (S-27) as a yellow oil. MS (ESI) m/z 432.2 $[M]^+$.

Step 6. To a mixture of 3-[2-biphenyl-2-yl-2-(4-methoxy-phenoxy)-acetoxy]-1,1-dimethyl-pyrrolidinium trifluoroacetate (S-27) (314 mg, 0.73 mmol) in $CH_3CN/H_2O$ (10 mL/10 mL) was added CAN (800 mg, 1.46 mmol). The resulting mixture was stirred at room temperature overnight. The mixture was concentrated and the residue was purified by prep-HPLC (0.1% TFA as additive) to provide 3-(2-Biphenyl-2-yl-2-hydroxy-acetoxy)-1,1-dimethyl-pyrrolidinium trifluoroacetate (Example 11). $^1H$ NMR (400 MHz, $D_2O$): 7.50-7.39 (m, 6H), 7.38-7.35 (m, 3H), 5.41 (s, 1H), 5.36 (br, 1H), 3.73-3.66 (m, 1H), 3.60-3.41 (m, 3H), 3.23-3.12 (m, 3H), 2.83-2.72 (m, 3H), 2.64-2.56 (m, 1H), 2.20-1.98 (m, 1H). MS (ESI) m/z 326.2 $[M]^+$.

Example 12. Synthesis of 3-(2-hydroxy-2-(2-isopropylphenyl)acetoxy)-1,1-dimethylpyrrolidin-1-ium chloride Example 12

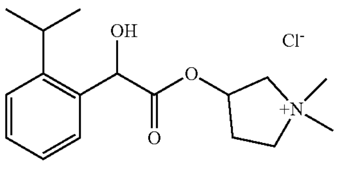

Scheme 6

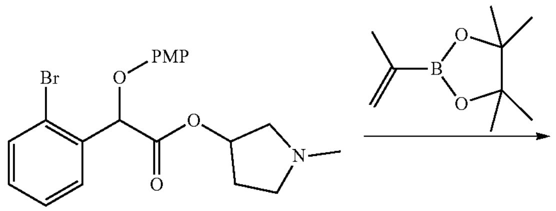

S-20

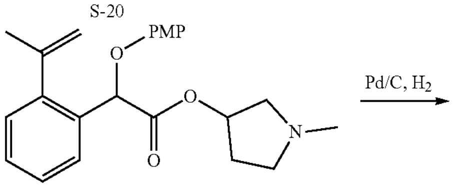

S-28

-continued

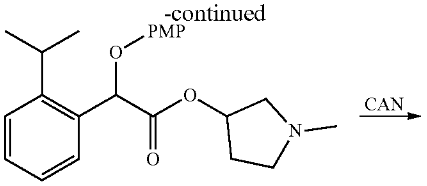

S-29

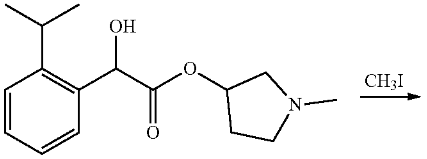

S-30

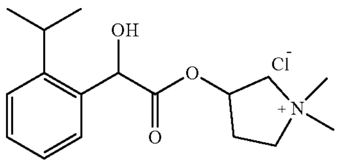

Example 12

Step 1. A mixture of 1-methylpyrrolidin-3-yl 2-(2-bromophenyl)-2-(4-methoxyphenoxy)acetate (S-20) (500 mg, 1.19 mmol), 4,4,5,5-tetramethyl-2-(prop-1-en-2-yl)-1,3,2-dioxaborolane (240 mg, 1.43 mmol), $K_2CO_3$ (328 mg, 2.38 mmol) and $Pd(PPh_3)_4$ (137 mg, 0.12 mmol) in dioxane/$H_2O$ (10 mL/1 mL) was stirred at 100° C. under $N_2$ overnight. The reaction mixture was diluted with water (20 mL) and extracted with EA (20 mL×2). The combined organic phases were washed with brine, dried with $Na_2SO_4$, and filtered. The filtrate was concentrated and the residue was purified by silica-gel column chromatography eluting with EA to give 1-methylpyrrolidin-3-yl 2-(4-methoxyphenoxy)-2-(2-(prop-1-en-2-yl)phenyl)acetate (S-28). MS (ESI) m/z 382.2 [M+H]+.

Step 2. To a solution of 1-methylpyrrolidin-3-yl 2-(4-methoxyphenoxy)-2-(2-(prop-1-en-2-yl)phenyl)acetate (S-28) (300 mg, 0.78 mmol) in MeOH (5 mL) was added Pd/C (80 mg). And the mixture was stirred at room temperature under $H_2$ for 4 h. The reaction mixture was filtered and the filtrate was concentrated to give 1-methylpyrrolidin-3-yl 2-(2-isopropylphenyl)-2-(4-methoxyphenoxy)acetate (S-29). MS (ESI) m/z 384.2 $[M+H]^+$.

Step 3. To a mixture of 1-methylpyrrolidin-3-yl 2-(2-isopropylphenyl)-2-(4-methoxyphenoxy)acetate (S-29) (270 mg, 0.71 mmol) in $CH_3CN$/H2O (5 mL/5 mL) was added CAN (1.16 g, 2.11 mmol). The reaction mixture was stirred at room temperature overnight. The reaction mixture was concentrated. Then the residue was diluted with water (10 mL) and extracted with EA (20 mL). The aqueous solution was adjusted to pH 9 using $Na_2CO_3$ solution. The resulting mixture was extracted with EA (20 mL×2). The combined organic phases were washed with brine, dried over $Na_2SO_4$, filtered. The filtrate was concentrated to give 1-methylpyrrolidin-3-yl 2-hydroxy-2-(2-isopropylphenyl)acetate (S-30) as a brown solid, which was used to next step without further purification. MS (ESI) m/z 278.2 $[M+H]^+$.

Step 4. To a mixture of 1-methylpyrrolidin-3-yl 2-hydroxy-2-(2-isopropylphenyl)acetate (S-30) (100 mg, 0.29 mmol) in 2-butanone (2 mL) was added $CH_3I$ (1 mL). The mixture was stirred at 65° C. for 2 h. The reaction mixture was concentrated to give crude product. And the crude was purified by prep-HPLC (0.1% TFA as additive), The product was treated with HCl and lyophilizated to give 3-(2-hydroxy-2-(2-isopropylphenyl)acetoxy)-1,1-dimethylpyrrolidin-1-ium chloride, Example 12. $^{1}H$ NMR (400 MHz, $D_2O$): 7.44 (d, J=8 Hz, 1H), 7.40-7.35 (m, 1H), 7.27-7.22 (m, 2H), 5.71 (d, J=9.2 Hz, 1H), 5.54 (br, 1H), 3.83-3.71 (m, 2H), 3.64-3.45 (m, 2H), 3.31-3.21 (m, 1H), 3.13, 3.08 (s, 3H), 2.90, 2.73 (s, 3H), 2.71-2.66 (m, 1H), 2.34-2.30 (m, 1H), 2.13-2.06 (m, 1H), 1.24-1.13 (m, 6H). MS (ESI) m/z 292.2 $[M]^+$.

Biological Example 1. In Vitro Assay for Determining IC50

FLIPR assay was used to evaluate the potency of compounds. CHO-K1 cells stably expressing M3 receptor were cultured at 37° C. in the culture media (90% Ham's F-12 Nutrient Mixture, Gibco; 10% fetal bovine serum, Biosera; 200 μg/mL Hygromycin, and Penicillin (100 U/mL)/Streptomycin (100 μg/mL), Invitrogen) till 100% confluency in cell culture incubator (ThermoFisher, 5% $CO_2$). Cells were harvested by using 0.25% Trypsin/EDTA, spun down at 300×g for 5 min, and resuspended in the culture media at cell density of $5\times10^5$ cells/mL. Twenty microliter of cell suspension (10,000 cells/well) was transferred to 384-well plate and cultured for 24 hr before assay. DMSO was used as blank control and scopolamine (MedChemExpress) as a positive control for antagonist. Compounds were prepared in DMSO (stock concentration: 1 mM) and 3× serially diluted (10 concentrations) in 384-LDV plate (Labcyte). Ninety nL of serially diluted compounds were transferred from 384-LDV plate into compound plate (PerkinElmer) by Echo 550 (Labcyte), and 30 uL assay buffer (1×HBSS with 20 mM HEPES, pH 7.4, Sigma) were added to each well. For FLIPR assay, culture media was removed and 20 uL of 1× loading dye (Assay buffer with 2 μM Fluo-8 AM, AAT Bioquest; 1 mM Probenecid and 0.0025% pluronic F-127, Sigma) was added to each well. The plate was incubated at 37° C. for 1 hr (avoid light exposure). For FLIPR assay, Excitation wavelength was set at 470/495 nm and Emission wavelength was set at 515/575 nm (Molecular Devices). Assay was performed in both agonist and antagonist modes. For agonist mode, 10 μL of diluted compounds were transferred to cell culture well and incubated at room temperature for 10 min. For antagonist mode, 10 μL diluted compounds with 8 nM acetylcholine (EC80, MedChemExpress) was added to each well, incubated at room temperature for 10 min. RFU value was calculated by subtracting minimum from maximum of FLIPR signal. Inhibitory effect of compounds on acetylcholine-induced calcium flux was calculated by % Effect=$(RFU_{sample}-RFU_{DMSO})/(RFU_{Scopolamine}-RFU_{DMSO})\times100$. Dose response curve fitting and $IC_{50}$ value of each compound was calculated by using XLFit. The following table lists the IC50 where * means IC50>1000 nM;  10-100 nM; *<10 nM.

| Compound | IC50 |
|---|---|
| Example 1 | ** |
| Example 2 | *** |
| Example 3 | ** |
| Example 4 | ** |
| Example 5 | ** |
| Example 6 | *** |
| Example 7 | ** |
| Example 8 | ** |
| Example 9 | *** |
| Example 10 | ** |

-continued

| Compound | IC50 |
|---|---|
| Example 11 | ** |
| Exampe 12 | * |

The Summary an Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

With respect to aspects of the invention described as a genus, all individual species are individually considered separate aspects of the invention. If aspects of the invention are described as "comprising" a feature, embodiments also are contemplated "consisting of" or "consisting essentially of" the feature.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference. To the extent that any meaning or definition of a term in this document conflicts with any meaning or definition of the same term in a document incorporated by reference, the meaning or definition assigned to that term in this document shall govern.

What is claimed is:

1. A salt having Formula I:

Formula I

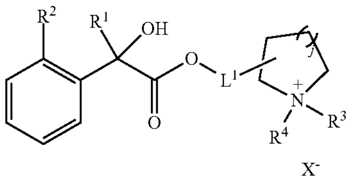

wherein:

$X^-$ is a counterion;

$R^1$ is hydrogen;

$L^1$ is null, $C_{1-4}$ alkylene, or $C_{1-4}$ heteroalkylene;

$R^2$ is $C_{3-8}$ carbocyclyl, 4-8 membered heterocyclyl, phenyl, or 5-10 membered heteroaryl, each of which is optionally substituted;

$R^3$ and $R^4$ are each independently hydrogen or $C_{1-6}$ alkyl; and j is 0, 1 or 2.

2. The salt of claim 1, which has a formula according to Formula I-1 or Formula I-2:

Formula I-1

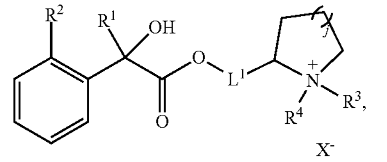

Formula I-2

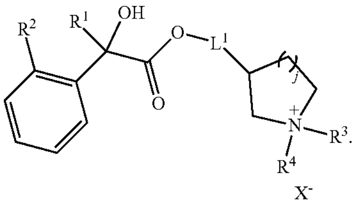

3. The salt of claim 1, wherein $L^1$ is null or a $C_{1-4}$ alkylene.

4. The salt of claim 1, wherein $L^1$ is $CH_2$.

5. The salt of claim 1, wherein $R^2$ is $C_{3-6}$ cycloalkyl, which is optionally substituted with one or more substituents independently selected from F, OH, $R^A$, and $OR^A$, wherein $R^A$ at each occurrence is independently a $C_{1-4}$ alkyl or $C_{3-6}$ cycloalkyl, which is optionally substituted with one or more substituents independently selected from F, OH, $C_{1-4}$ alkyl, fluorine-substituted $C_{1-4}$ alkyl, $C_{1-4}$ alkoxy, and fluorine-substituted $C_{1-4}$ alkoxy; (ii) $C_{4-7}$ cycloalkenyl, such as cyclopentenyl, which is optionally substituted with one or more substituents independently selected from F, OH, $R^A$, and $OR^A$, wherein $R^A$ at each occurrence is independently a $C_{1-4}$ alkyl or $C_{3-6}$ cycloalkyl, which is optionally substituted with one or more substituents independently selected from F, OH, $C_{1-4}$ alkyl, fluorine-substituted $C_{1-4}$ alkyl, $C_{1-4}$ alkoxy, and fluorine-substituted $C_{1-4}$ alkoxy; (v) (iii) phenyl, which is optionally substituted with one or more substituents independently selected from F, Cl, OH, $C_{1-4}$ alkyl, fluorine-substituted $C_{1-4}$ alkyl, $C_{1-4}$ alkoxy, and fluorine-substituted $C_{1-4}$ alkoxy; (iv) a 5-membered heteroaryl having 1-3 ring heteroatoms independently selected from N, O, and S, which is optionally substituted with one or more substituents independently selected from F, Cl, OH, $C_{1-4}$ alkyl, fluorine-substituted $C_{1-4}$ alkyl, $C_{1-4}$ alkoxy, and fluorine-substituted $C_{1-4}$ alkoxy; or (v) a 6-membered heteroaryl having 1-2 ring heteroatoms independently selected from N, O, and S, which is optionally substituted with one or more substituents independently selected from F, Cl, OH, $C_{1-4}$ alkyl, fluorine-substituted $C_{1-4}$ alkyl, $C_{1-4}$ alkoxy, and fluorine-substituted $C_{1-4}$ alkoxy.

6. The salt of claim 1, wherein $R^3$ is methyl.

7. The salt of claim 1, wherein $R^4$ is methyl.

8. The salt of claim 1, wherein j is 1.

9. The salt of claim 1, wherein $X^-$ is a pharmaceutically acceptable counterion.

10. A salt selected from those shown in Table 1 or 2, wherein $X^-$ is a pharmaceutically acceptable counterion:

TABLE 1

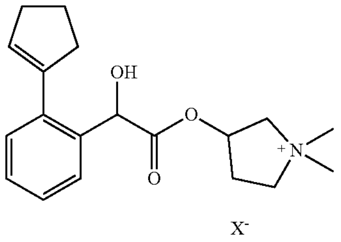

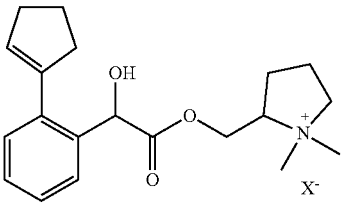

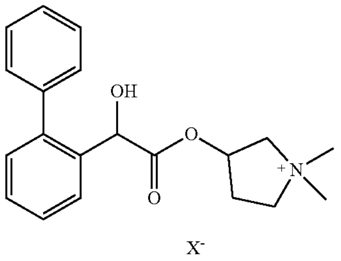

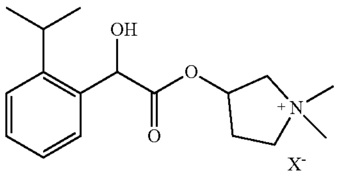

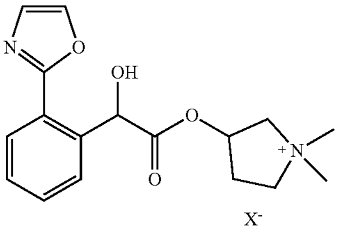

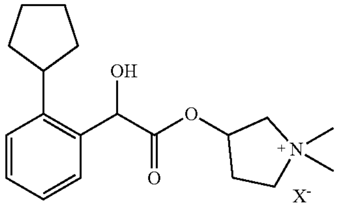

TABLE 1-continued
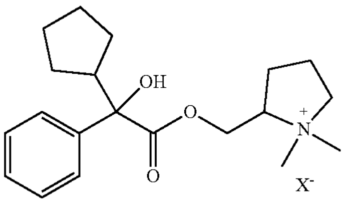
TABLE 2
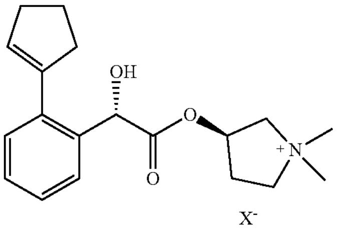
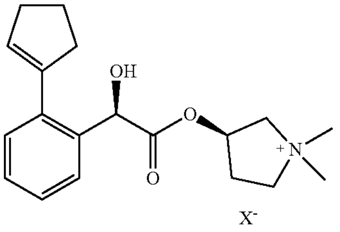
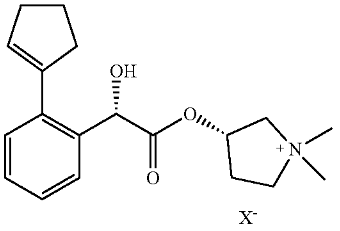
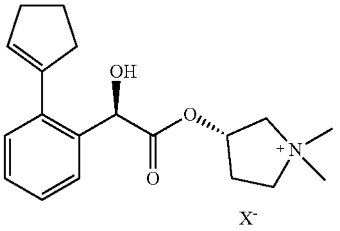
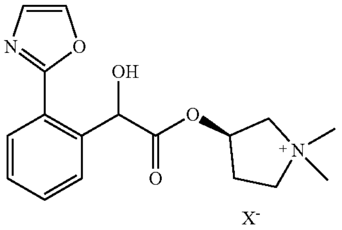
TABLE 2-continued
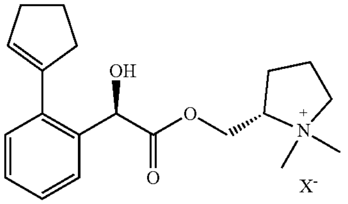
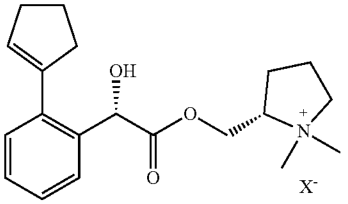
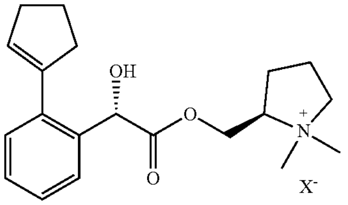
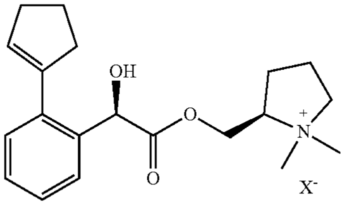
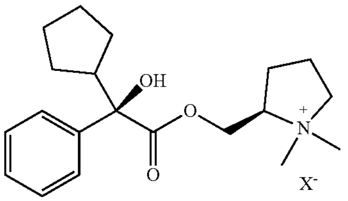
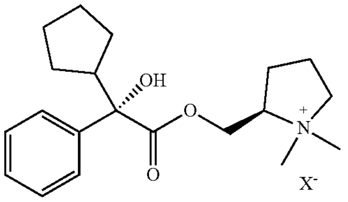
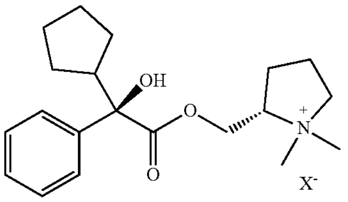

TABLE 2-continued

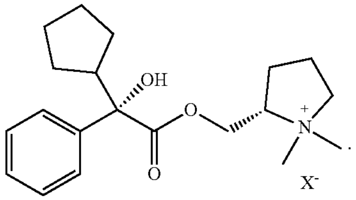

11. A pharmaceutical composition comprising the salt of claim 9 and optionally a pharmaceutically acceptable carrier.

12. The pharmaceutical composition of claim 11, which is formulated for topical administration.

13. The pharmaceutical composition of claim 11, which is in the form of a topical solution, cream, ointment, mousse, gel, lotion, or powder.

14. A method of treating hyperhidrosis, reducing drooling, reducing secretions in stomach or airway, protecting heart and nervous system, treating chronic obstructive pulmonary disease, inducing pupil dilation, or treating abdominal pain in a subject in need thereof, comprising administering to the subject a therapeutically effective amount of the salt of claim 9.

15. The method of claim 14, wherein the method is for treating hyperhidrosis, and the administering is a topical administration.

16. A compound having Formula II, or a salt thereof:

Formula II

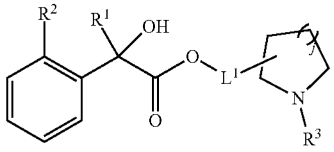

wherein:

$R^1$ is hydrogen;

$L^1$ is null, $C_{1-4}$ alkylene, or $C_{1-4}$ heteroalkylene;

$R^2$ is $C_{1-6}$ alkyl, $C_{2-6}$ alkenyl, $C_{2-6}$ alkynyl, $C_{3-8}$ carbocyclyl, 4-8 membered heterocyclyl, phenyl, or 5-10 membered heteroaryl, each of which is optionally substituted;

$R^3$ is hydrogen or $C_{1-6}$ alkyl; and j is 0, 1 or 2.

17. The compound of claim 16, or a salt thereof, which has a formula according to Formula II-1 or Formula II-2:

Formula II-1

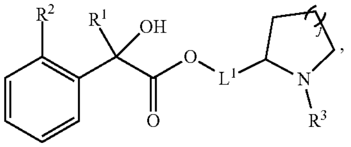

Formula II-2

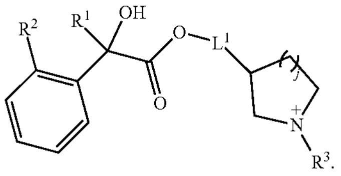

18. The salt of claim 5, wherein $L^1$ is $CH_2$.

19. The salt of claim 18, wherein j is 1.

* * * * *